US009526433B2

(12) United States Patent
Lapetina et al.

(10) Patent No.: US 9,526,433 B2
(45) Date of Patent: Dec. 27, 2016

(54) WRIST-MOUNTED ELECTROCARDIOGRAPHY DEVICE

(71) Applicant: Verily Life Sciences LLC, Mountain View, CA (US)

(72) Inventors: John Lapetina, Los Altos Hills, CA (US); Russell Norman Mirov, Los Altos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 227 days.

(21) Appl. No.: 14/485,392

(22) Filed: Sep. 12, 2014

(65) Prior Publication Data

US 2016/0073914 A1 Mar. 17, 2016

(51) Int. Cl.
*A61B 5/0408* (2006.01)
*A61B 5/00* (2006.01)

(52) U.S. Cl.
CPC ........... *A61B 5/04085* (2013.01); *A61B 5/681* (2013.01); *A61B 5/6824* (2013.01); *A61B 2560/0443* (2013.01)

(58) Field of Classification Search
CPC ... A61B 5/0408; A61B 5/04085; A61B 5/681; A61B 5/6824
USPC ................................................. 600/390, 509
See application file for complete search history.

(56) References Cited

U.S. PATENT DOCUMENTS

| | | | | | |
|---|---|---|---|---|---|
| 4,120,294 | A | * | 10/1978 | Wolfe | A61B 5/024 600/384 |
| 4,230,127 | A | * | 10/1980 | Larson | A61B 5/0404 600/382 |
| 4,248,244 | A | * | 2/1981 | Charnitski | A61B 5/0404 600/519 |

(Continued)

FOREIGN PATENT DOCUMENTS

| | | |
|---|---|---|
| EP | 0861045 B1 | 8/2002 |
| KR | 10-2009-0099147 A | 9/2009 |

OTHER PUBLICATIONS

International Search Report and Written Opinion of International Application No. PCT/US2015/048311 dated Dec. 17, 2015 (mailed Dec. 17, 2015).

(Continued)

*Primary Examiner* — Lee S Cohen
(74) *Attorney, Agent, or Firm* — McDonnell Boehnen Hulbert & Berghoff LLP

(57) ABSTRACT

Wearable devices are described herein including a housing and a mount configured to mount the housing to a wrist of a wearer. The wearable devices further include first and second electrical contacts configured such that the first electrical contact is in contact with skin proximate of the wrist when the wearable device is so mounted. The second electrical contact is disposed on a surface of the wearable device away from the wrist such that, when the wearer contacts the second electrical contact with a finger or other element of the arm opposite the wrist, an electrocardiographic waveform of the wearer can be extracted from (Continued)

voltage fluctuations between the first and second electrodes. Such wearable devices can be used for periodic logging or other applications of the electrocardiographic waveforms of the wearer. Such logged electrocardiographic waveforms could be used to determine a medical or health state of the wearer.

20 Claims, 11 Drawing Sheets

(56) References Cited

U.S. PATENT DOCUMENTS

| | | | | |
|---|---|---|---|---|
| 4,513,753 | A * | 4/1985 | Tabata | A61B 5/0404 600/519 |
| 5,738,104 | A | 4/1998 | Lo et al. | |
| 5,876,350 | A | 3/1999 | Lo et al. | |
| 6,950,695 | B2 * | 9/2005 | Chen | A61B 5/02438 600/509 |
| 7,171,259 | B2 * | 1/2007 | Rytky | A61B 5/02438 600/509 |
| 7,894,888 | B2 * | 2/2011 | Chan | A61B 5/0006 600/509 |
| 8,369,936 | B2 | 2/2013 | Farringdon et al. | |
| 2009/0312655 | A1 | 12/2009 | Lo | |
| 2009/0312656 | A1 | 12/2009 | Lau et al. | |
| 2010/0145202 | A1 * | 6/2010 | Mclaughlin | G06K 9/0053 600/509 |
| 2011/0066010 | A1 | 3/2011 | Moon et al. | |
| 2013/0261405 | A1 | 10/2013 | Lee et al. | |
| 2014/0257049 | A1 * | 9/2014 | Soundarapandian | A61B 5/681 600/301 |
| 2014/0268522 | A1 * | 9/2014 | Tanaka | A61B 5/681 361/679.01 |
| 2014/0323818 | A1 * | 10/2014 | Axelgaard | A61B 5/0022 600/301 |
| 2014/0336493 | A1 * | 11/2014 | Kulach | A61B 5/04085 600/390 |
| 2015/0091764 | A1 * | 4/2015 | Hsieh | H01Q 5/364 343/702 |
| 2015/0164422 | A1 * | 6/2015 | Lee | A61B 5/6831 600/301 |
| 2015/0173632 | A1 * | 6/2015 | Ma | A61B 5/14552 600/324 |
| 2015/0223709 | A1 * | 8/2015 | Lee | A61B 5/02438 600/384 |
| 2016/0062417 | A1 * | 3/2016 | Chu | G06F 1/1698 600/390 |

OTHER PUBLICATIONS

Analog Devices, Inc., Data Sheet for AD8232, "Single-Lead, Heart Rate Monitor Front End," 2012, 28 pages.
Broeders, Jan-Hein, "Predicting and Finding your Limits!," Technical Article MS-2385, Analog Devices, Inc., 2012, 3 pages.
Oregon Scientific, Heart Rate Monitor Watch with Calorie Counter, Model: IHM80004, User Manual, 2010, 2 pages.
Oregon Scientific, Touch Strapless Heart Rate Monitor, Model: SE338/SE338M, User Manual, 2011, 2 pages.
Sportline, Inc., Solo 910 Heart Rate Watch, 2006, 18 pages.

* cited by examiner

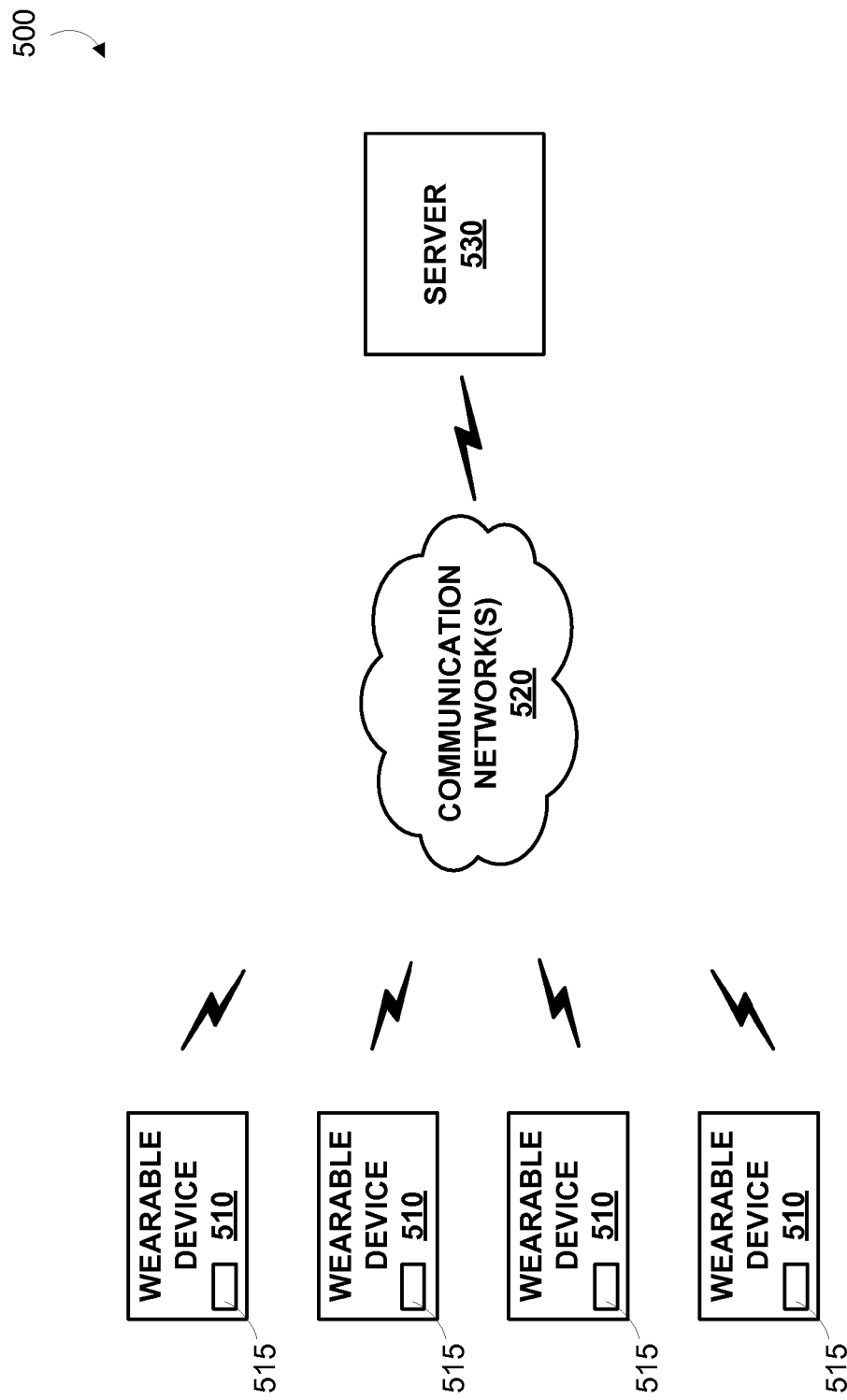

WRIST-MOUNTED ELECTROCARDIOGRAPHY DEVICE

BACKGROUND

Unless otherwise indicated herein, the materials described in this section are not prior art to the claims in this application and are not admitted to be prior art by inclusion in this section.

Electrocardiography (ECG) is a technique that records electrical activity of the heart by measuring electrical signals from two or more points on the skin. The measurements result in one or more waveforms (electrocardiograms) that are related to the beating of the heart. The waveforms may also include other features that may be indicative of heart health, abnormalities, or medical conditions. The electrocardiographic measurements can be obtained by placing electrodes on the skin at multiple body locations (e.g., on the chest, arms, and/or legs) and electrically connecting the electrodes to a heart monitor or other electronic measurement device. Typically, electrocardiograms are obtained in clinical settings in which a physician, nurse, or other medical professional is involved in placing the electrodes on the body and operating the heart monitor.

SUMMARY

Some embodiments of the present disclosure provide a wearable device including: (i) a housing; (ii) a mount configured to mount the housing to a first external body surface, wherein the first external body surface is a wrist location of a first arm of a wearer; (iii) a first electrical contact disposed on the housing, wherein the first electrical contact is configured to contact skin at the first external body surface when the housing is mounted on the first external body surface; (iv) a second electrical contact, wherein the second electrical contact is configured to be contacted by skin of a second external body surface, wherein the second external body surface is a location of a second arm of the wearer; and (v) a signal conditioner disposed in the housing and electrically connected to the first and second electrical contacts, wherein the signal conditioner is configured to extract an electrocardiographic waveform from voltage fluctuations between the first electrical contact and the second electrical contact.

Some embodiments of the present disclosure provide a wearable device including: (i) a housing; (ii) means for mounting the housing to a first external body surface, wherein the first external body surface is a wrist location of a first arm of a wearer; (iii) a first electrical contact disposed on the housing, wherein the first electrical contact is configured to contact skin at the first external body surface when the housing is mounted on the first external body surface; (iv) a second electrical contact, wherein the second electrical contact is configured to be contacted by skin of a second external body surface, wherein the second external body surface is a location of a second arm of the wearer; and (v) means for extracting an electrocardiographic waveform from voltage fluctuations between the first electrical contact and the second electrical contact.

Some embodiments of the present disclosure present a method including: (i) mounting a wearable device to a wrist location of a first arm of a wearer, wherein the device comprises: (a) a housing; (b) a mount configured to mount the housing to the wrist location; (c) a first electrical contact disposed on the housing, wherein the first electrical contact is configured to contact skin at a first external body surface when the housing is mounted on the first external body surface; (d) a second electrical contact, wherein the second electrical contact is configured to be contacted by skin of a second external body surface, wherein the second external body surface is a location of a second arm of the wearer; and (e) a signal conditioner disposed in the housing and electrically connected to the first and second electrical contacts, wherein the signal conditioner is configured to extract an electrocardiographic waveform from voltage fluctuations between the first electrical contact and the second electrical contact; (ii) while the wearable device is mounted to the wrist location of the first arm of the wearer such that the first electrical contact is in contact with skin at the first external body surface, placing skin of the second external body surface in contact with the second electrical contact; and (iii) while the first electrical contact is in contact with skin at the first external body surface and the second electrical contact is in contact with skin of the second external body surface, using the signal conditioner to extract the electrocardiographic waveform.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 5 is a block diagram of an example system that includes a plurality of wearable devices in communication with a server.

DETAILED DESCRIPTION

Figure 1A:
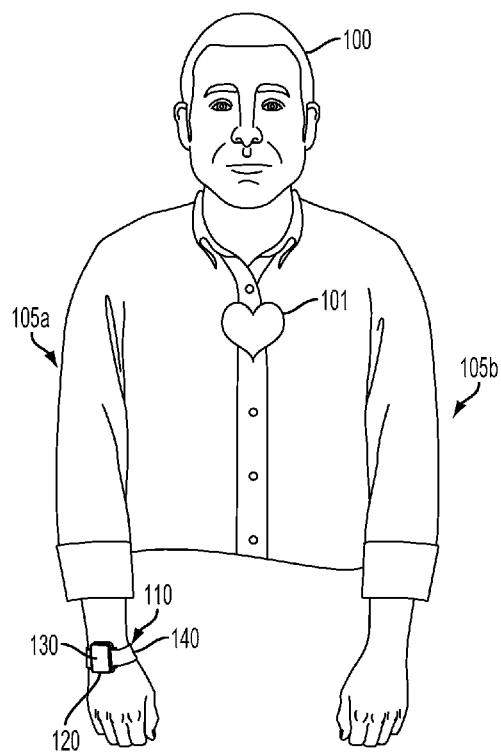
FIG. 1A is a view of a person wearing an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A wearable device may be configured to measure one or more physiological parameters of the wearer. The one or more physiological parameters can include an electrocardiographic waveform (ECG), which may be related to the electrical activity of the wearer's heart and, thus, a medical and/or health state of the wearer. To measure an ECG waveform, the wearable device may include two electrical contacts that can be placed in contact with the wearer's skin at respective locations such as the wearer's wrist(s), forearm(s), upper arm(s), leg(s), thigh(s), etc. For example, first and second electrical contacts could contact skin on the left and right arms of the wearer, respectively (e.g., skin at the left and right wrists of the wearer, skin at the left wrist and right index finger of the wearer, etc.), and the ECG waveform may be extracted from voltage fluctuations between the first and second electrical contacts. One or more properties of a detected ECG waveform and/or of a plurality of detected ECG waveforms (detected, e.g., during a plurality of respective periods of time) could be determined and/or related to one or more physiological and/or health states of the wearer.

In some examples, the wearable device includes a housing (e.g., a water-resistant and/or water-proof housing) and a mount (e.g., a band) that can mount the housing on a particular external body location, such as a wrist of a first arm of the wearer (i.e., a first external body surface). The first electrical contact may protrude from a side of the housing facing the skin at the wrist location of the first arm, such that the first electrical contact contacts the skin of the wrist location when the housing is mounted on the wrist. The second electrical contact could be configured to be contacted by skin at a location on a second arm of the wearer (e.g., skin of a finger, hand, wrist, or other location on the arm of the wearer opposite the arm to which the wearable device is mounted). For example, the second electrical contact could be disposed on an outside surface of the housing and/or the mount (e.g., an outside surface of a band used to mount the wearable device to the wrist of the first arm) such that the wearer could move his or her second arm (i.e., the arm opposite the arm to which the wearable device is mounted) to touch the second electrical contact without the second arm being in electrical contact with the first arm. When the wearable device is operated in this way, a signal conditioner or other electronics of the wearable device may extract an ECG waveform from voltage fluctuations between the first and second electrical contacts. The wearable device could be used to extract such ECG waveforms while the wearer is involved in certain activities (e.g., while running or engaged in other forms of exercise) or throughout the day. Thus, the wearable device may facilitate repeated and/or near-continuous cardiac monitoring. Such cardiac monitoring could allow the detection of rare events (e.g., arrhythmias, transient bradycardia and/or tachycardia), cardiac electrical activity during a wider range of wearer behaviors than occur in a hospital or other controlled medical setting, the detection of changes in the electrical activity of the heart over protracted (e.g., weeks, months) periods of time, or other properties of the physiological state of a wearer.

The electronics of the wearable device may include a signal conditioner, a microprocessor, an analog-to-digital converter (which may be part of the microprocessor), data storage, a wireless transmitter, and/or other components. The signal conditioner may be electrically connected to the first and second electrical contacts and may be configured to extract an ECG waveform from voltage fluctuations between the electrical contacts. The signal conditioner may, for example, include at least one amplifier, at least one high-pass filter, and at least one low-pass filter. The microprocessor may obtain data related to the electrocardiographic signal (e.g., after the signal is digitized by the analog-to-digital converter), and the microprocessor may use the wireless transmitter to transmit the data related to the ECG waveform to a remote computing device (e.g., to the "cloud"). Additionally or alternatively, the microprocessor may log the data related to the ECG waveform in the data storage. In some examples, the electronics (e.g., the signal conditioner) includes circuitry or other elements configured to detect that the first and second electrical contacts are contacting skin and/or that an ECG waveform may be extracted from voltage fluctuations between the electrical contacts. The wearable device may be operated relative to such a determination; for example, an ECG waveform may be extracted using the signal conditioner and logged, transmitted, or used in some other way in response to the determination that the first and second electrical contacts are in contact with skin at respective first and second skin locations.

The first and second electrical contacts (and any further electrical contacts) of the wearable device could be configured in a variety of ways to allow the extraction of an ECG waveform from voltage fluctuations between the electrical contacts under a range of physiological and environmental conditions. The electrodes could have a variety of surface compositions to allow ohmic and/or capacitive electrical coupling between the electrodes and skin locations of a wearer. Such surface compositions could include stainless steel, gold, platinum, silver, silver/silver-chloride, polymers or rubbers containing conductive particles, or other conductive or partially conductive materials. Further, the shape and/or surface texture of the electrodes could be specified to allow electrical contact with skin. In some examples, the electrodes could be configured to have a substantially capacitive electrical contact with skin; e.g., the electrodes could include a flat conductor having a substantially non-conductive dielectric coating configured to be in contact with skin. Other compositions and configurations of electrodes are anticipated.

The wearable device could include further sensors. In some examples, this could include the wearable device having additional electrical contacts configured to provide additional electrophysiological signals (e.g., EMG signals) or other information (e.g., skin resistance, Galvanic skin response). Further sensors could include temperature sensors, light sensors, galvanic sensors, proximity sensors, GPS sensors, accelerometers, or other sensors or combinations of sensors. In some examples, the device could include a photoplethysmographic sensor or some other sensor(s) configured to detect a volume and/or a change in the volume of blood in subsurface vasculature of a wearer. Such detected information could be used, in combination with an extracted ECG waveform, to determine one or more properties of the heart and/or vasculature of the wearer. For example, a diastolic, systolic, or other blood pressure of the wearer could be determined.

In some examples, the wearable device may include a user interface that is configured to provide user-discernible indications (e.g., visual, audible, and/or tactile indications) of one or more physiological parameters measured and/or determined by the device. For example, the user interface could indicate an ECG waveform extracted using the first and second electrical contacts during a period of time when the user is contacting the second electrode with, e.g., a finger of an arm opposite the arm to which the wearable device is mounted. In some examples, the user interface could additionally provide a means for one or more settings of the wearable device (e.g., a frequency at which to operate the user interface to indicate that the user should contact the second electrical contact with, e.g., a finger of the opposite arm) to be specified by a wearer according to the wearer's preferences. In some examples, the wearable device may include a wireless communication interface that can transmit data to an external device, for example, using Bluetooth, ZigBee, WiFi, and/or some other wireless communication protocol. The data transmitted by the wireless communication interface may include data indicative of one or more physiological parameters measured by the device, such as extracted ECG waveforms.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. ECG Performed Between the Arms of a Wearer

The heart creates an electric field within the body during the process of pumping blood. The temporal and spatial properties of this field are related to the sum of a plurality of ionic currents that flow within the heart as a result of the depolarization and repolarization of electrically active cells of the heart (e.g., cardiomyocytes) during activity of the heart (e.g., during a heartbeat). This electric field within the body results in voltage fluctuations at the skin (and other locations within the body) being related at least in part to the electrical activity of the heart. As a result, measurement of these voltage fluctuations could be used to detect and/or determine information about the activity of the heart, e.g., to determine a health or medical state (e.g., a disease state) of the heart.

An electrocardiographic (ECG) waveform can be extracted from voltage fluctuations between two (or more) location on the skin of a person (e.g., by using electrodes to grant a measurement device electrical access to the two or more skin locations). ECG waveforms can be extracted from pairs of skin locations on a person, such as between the left and right arms, between the right arm and left leg, and between the left arm and left leg. ECG waveforms can also be extracted from combinations of voltage fluctuations at more than two skin locations; for example, an ECG waveform could be generated based on the difference between the voltage at a first electrode (e.g., an electrode over the heart) and a mean of the voltages of a set of other electrodes (e.g., a mean over the voltages of electrodes at the right arm, left arm, and left leg).

Further, an extracted ECG waveform corresponding to a particular heartbeat generally includes a number of temporal features corresponding to phases of the activity of the heart during the particular heartbeat. Specifically, such an extracted ECG waveform may include a P wave (corresponding to depolarization of the atria of the heart), QRS complex (corresponding to depolarization of the ventricles of the heart), and a T wave (corresponding to repolarization of the ventricles). Such an extracted ECG waveform may include additional features (e.g., a U wave) and/or lack features (e.g., the T wave) according to a medical state of a person, an anatomical or physiological property of the person, and/or the properties of the electrodes and/or measurement equipment used to extract the ECG waveform. One or more properties of the extracted ECG waveform (e.g., a Q-T interval, an R-R interval, a P-R interval, an S-T interval, a Q-T interval, an amplitude and/or polarity of a T-wave, and amplitude, polarity, or some other parameter(s) of some other aspect of the ECG waveform) could be determined and used to determine a medical and/or health state of the heart and/or of the person containing the heart (e.g., a metabolic rate, a degree of physical exertion, an elevated or depressed level of one or more electrolytes, coronary ischemia, heart attack, cardiac hypertrophy, the presence of certain drugs and/or toxins).

A wearable device could be configured to extract one or more ECG waveforms from skin of a wearer by measuring voltage fluctuations between two or more skin locations of the wearer. This could include accessing the voltage fluctuations at the two or more skin locations by applying respective two or more electrical contacts or electrodes to the two or more skin locations, and electrically connecting the two or more electrical contacts or electrodes to a signal conditioner or other electrical measurement device of the wearable device. This connection could include long flexible leads connecting between a particular skin location to the wearable device, which could be located at some other location on or near the body of the wearer (e.g., the wearable device could be connected to a belt worn by the wearer, and leads could run from the belt location to electrical contacts at two skin locations at the wrists of the wearer). Additionally or alternatively, two or more electrical contacts could be disposed on the wearable device and configured to contact respective two or more skin locations. The two or more skin locations could be proximate to each other (e.g., the wearable device could be mounted to a wrist of the wearer, and the two skin locations could be skin location on the wrist of the wearer). Alternatively, the two or more skin locations could be distant locations and the wearer could move skin locations of the wearer's body to contact electrical contacts of the wearable device.

As an example, a wearable device could be configured to mount to a first wrist (e.g., the left wrist) of the wearer and to have a first electrical contact configured to contact a first skin location on the first wrist. The wearable device could further include a second electrical contact configured to be contacted by a second skin location of the wearer. That is, the wearer could move a portion of the wearer's body (e.g., a right hand) proximate to the wearable device such that a second skin location (e.g., a finger, hand, or wrist location of the arm of the wearer opposite the arm to which the wearable device is mounted) is in contact with the second electrical contact of the wearable device. In this way, the wearable device could enable periodic extraction of ECG waveforms from voltage fluctuations between the two skin locations (e.g., between a wrist location of the left arm and a finger location of the right arm). Such a wearable device could be configured in the form of a wristwatch or other wrist-mounted device (i.e., having a central housing (on or within which could be mounted first and/or second electrical contacts) mounted to the wrist by e.g., a strap or band configured to encircle the wrist) and could include means for performing additional functions, e.g., indicating a time and/or information about extracted ECG waveforms to the wearer.

FIG. 1A illustrates such an example wearable device 110 mounted to a wrist of a first arm 105a of a wearer 100 during a first period of time. The wearable device 110 includes a housing 120 mounted to the wrist of the first arm 105a by a mount 140 (e.g., a strap or band). The wearable device further includes first (not shown) and second 130 electrical contacts. The first electrical contact is disposed on an inside (i.e., wrist-facing) side of the housing 120 and configured to contact skin at a first external body surface (i.e., skin of the wrist of the first arm 105a) when the housing 120 is mounted on the wrist of the first arm 105a. The second electrical contact 130 is configured to be contacted by skin of a second external body surface (e.g., by finger, hand, wrist, or other skin of a second arm 105b of the wearer 100). The wearable device 110 additionally includes electronics (e.g., a signal conditioner, not shown) electrically connected to the first and second 130 electrical contacts and configured to extract an ECG waveform (related to the electrical activity of the heart 101 of the wearer 100) from voltage fluctuations between the first and second 130 electrical contacts.

Figure 1B:
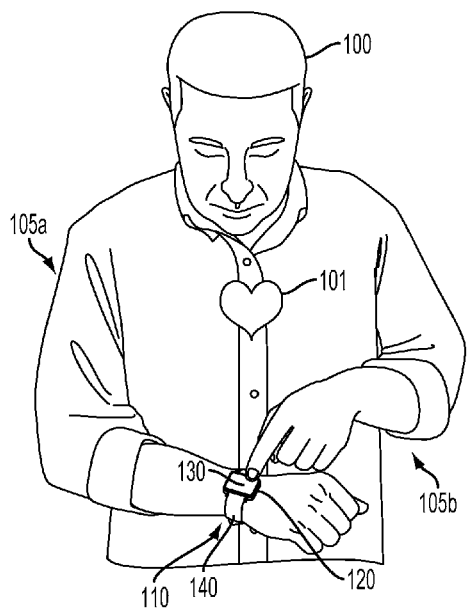
FIG. 1B is a view of the person and wearable device illustrated in FIG. 1A, when the user is contacting an electrical contact of the wearable device with a finger.

FIG. 1B illustrates the wearable device 110 and wearer 100 during a second period of time when the wearer 100 is positioning skin of a finger of the second arm 105b in contact with the second electrical contact 130. In this state, electronics (e.g., a signal conditioner) of the wearable device 110 could extract an ECG waveform related to the electrical activity of the wearer's 100 heart 101 during the second period of time from voltage fluctuations between the first and second 130 electrical contacts.

The wearer positioning skin of the finger (or some other location) of the second arm 105b proximate to the second electrical contact 130 could be performed a plurality of times to enable to extraction of ECG waveforms during a plurality of respective periods of time. The wearer positioning skin of the finger of the second arm 105b proximate to the second electrical contact 130 could be performed at the initiative of the wearer, e.g., in response to the wearer having performed and/or being about to perform a strenuous task (e.g., exercise), experiencing some symptoms (e.g., fatigue, nausea, vertigo, heart palpitations, orthostatic hypertension), having received and/or being about to receive a drug (e.g., having taken nitroglycerin). In some examples, the wearer could additionally operate the device to indicate some symptoms or other information related to an extracted ECG waveform. Additionally or alternatively, the wearer positioning skin of the finger of the second arm 105b proximate to the second electrical contact 130 could be performed in response to an indication (e.g., a vibration, a sound, a visual indication on a display of the device 100, an indication through some other device in communication with the wearable device 110) that the wearer should perform such an action to enable the extraction of an ECG waveform by the wearable device 110.

Figure 2:
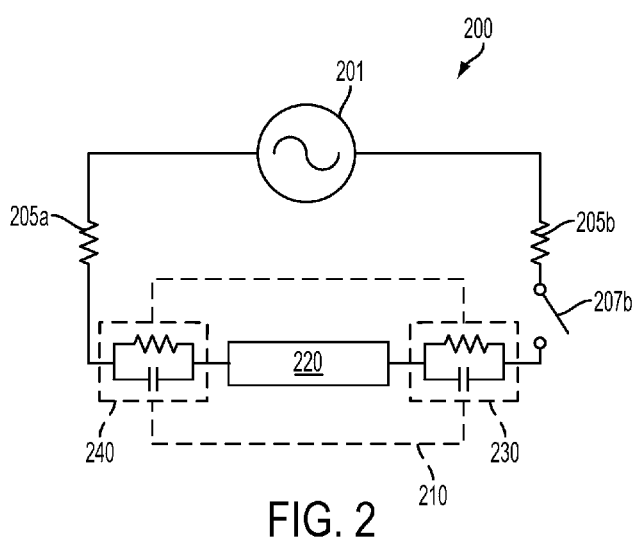
FIG. 2 is a diagram illustrating an example electrical model of elements of the person and wearable device illustrated in FIGS. 1A and 1B.

FIG. 2 illustrates an electrical circuit 200 modeling elements of the wearer 100 and wearable device 110 of FIGS. 1A and 1B. The electrical circuit 200 includes a time-varying voltage source 201 corresponding to the time-varying electrical field generated by the heart 101 of the wearer 100. The electrical circuit 200 additionally includes elements corresponding to the wearable device 110 (illustrated by bounding box 210). These elements 210 include equivalent resistor/capacitor networks 230, 240 corresponding to the electrical properties of the first and second 130 electrical contacts and their electrical coupling to respective first and second skin locations. The elements of the wearable device 210 additionally include a signal conditioner 220 electrically connected to the first 230 and second 240 electrical contacts and configured to extract an ECG waveform from voltage fluctuations between the first 240 and second 240 electrical contacts. The electrical circuit 200 further includes two resistors 205a, 205b representing the electrical properties (e.g., resistance to current flow) of the arms 105a, 105b and other tissue (e.g., chest tissue) between the heart 101 and the first and second 130 electrical contacts. A switch 207b represents the control-able electrical contact between the second electrical contact 130 and skin of the second arm 105b. Thus, the switch 207b is open to model the electrical behavior of the wearer 100 and wearable device 110 during the first period of time (corresponding to the scenario illustrated by FIG. 1A) and open to model the electrical behavior of the wearer 100 and wearable device 110 during the second period of time (corresponding to the scenario illustrated by FIG. 1B).

Thus, an ECG waveform extracted when the wearer 100 positions skin of the finger (or some other location) of the second arm 105b proximate to the second electrical contact 130 could correspond to a lead I ECG recording. That is, in embodiments wherein the wearable device 110 is mounted to a right wrist location and the signal conditioner extracts an ECG waveform by sensing the voltage fluctuations of the first electrical contact relative to the second electrical contact, the extracted ECG waveform corresponds to a lead I ECG recording. Alternatively, the wearable device 110 could be mounted to a left wrist location, and the extracted ECG waveform could correspond to an inverted lead I ECG recording. The user could indicate to the wearable device 110 (e.g., using a user interface of the wearable device 110) that the wearable device is mounted to a left (or right) wrist location. Additionally or alternatively, the wearable device 110 could determine that it is mounted to a left (or right) wrist location based on features (e.g., the polarity of the QRS complex) of an extracted ECG waveform.

Note that parameters of the electrical circuit 200 are related to electrical properties of the body of the wearer 100, of the first and second 130 electrical contacts, and to properties of the interface between the first and second 130 electrical contacts and respective first and second skin locations. Thus, the parameters of the electrical circuit 200 could be related to a dryness of other state of the skin locations, a type of skin at the skin locations, a degree of force applied between the skin locations and respective electrical contacts, or other considerations. Further, the parameters of the electrical circuit 200 could be related to the composition and configuration of the electrical contacts (e.g., a composition of a surface of the electrical contacts, a texture of the surface of the electrical contacts, a geometry of the electrical contacts). Correspondingly, one or more properties (e.g., an input impedance, a frequency response, a bandwidth, a sensitivity, a maximum input amplitude) of the signal conditioner 220 could be specified and/or controlled relative to expected values of those properties of the body of the wearer 100, of the first and second 130 electrical contacts, and/or of the interface between the first and second 130 electrical contacts and respective first and second skin locations (e.g., to allow the extraction of low-noise, high-amplitude, or otherwise optimized ECG waveforms).

Electrical contacts of the wearable device 110 could be configured in a variety of ways to allow the extraction of an ECG waveform from voltage fluctuations between the electrical contacts under a range of physiological and environmental conditions. The electrical contacts could have a variety of surface compositions to allow ohmic (i.e., related to conduction by ionic and/or redox reaction across the surface of the electrical contacts) and/or capacitive (i.e., related to the accumulation of opposite charges on opposite sides of a surface of the electrical contacts) electrical coupling between the electrodes and skin locations of a wearer. Such surface compositions could include stainless steel, gold, platinum, silver, silver/silver-chloride, polymers or rubbers containing conductive particles, or other conductive or partially conductive materials. Further, the shape and/or surface texture of the electrical contacts could be specified to control one or more properties of the electrical interface of the electrical contacts with skin. For example, the electrical contacts could have a specified large area in contact with skin, could protrude from a housing toward the skin (e.g., could have a rounded and/or pointed protruding geometry), could have a surface texture (e.g., to increase an effective surface area between a conductor of the electrical contact and fluids on the surface of the skin), or could be configured in some other way.

In some examples, the electrical contacts could be configured to have a substantially capacitive electrical contact with skin; that is, an electrical contact could engage in substantially no direct ionic and/or redox conduction across the interface between the electrical contact and the skin. Conduction of currents between such an electrode and the skin could instead consist substantially of the accumulation of opposite charges on respective opposite sides of a substantially nonconductive barrier between a conductor of the electrical contact and the skin. For example, an electrical contact could include a flat conductor having a substantially nonconductive dielectric coating configured to be in contact with skin. Additionally or alternatively, an electrical contact could have a textured conductive surface coated in a conformal layer of substantially nonconductive material. Other compositions and configurations of electrodes are anticipated.

A signal conditioner or other electronics of the wearable device 110 could include a variety of components configured in a variety of ways to allow one or more ECG waveforms to be extracted from voltage fluctuations between the first and second 130 electrical contacts when the first and second 130 electrical contacts are contacting appropriate respective skin locations of the wearer 100 and/or to allow other operations and applications. The electronics could include analog and/or digital electronic components to enable analog and/or digital manipulations of electrical signals related to voltage fluctuations between the electrical contacts. Generally, the electronics include components configured to amplify and filter voltage fluctuations between the electrical contacts (e.g., one or more amplifiers, buffers, filters, operational amplifiers, resistors, capacitors, inductors, transistors, rectifiers, or some other linear or nonlinear electronic component or combinations thereof).

For example, the electronics could be configured to generate an electronic signal (e.g., to generate an extracted ECG waveform) that is related to a band-passed version of the voltage fluctuations between the electrical contacts. This could include applying the voltage fluctuations to a band-pass filter having a pass-band between approximately 0.05 Hertz and approximately 150 Hertz. Additionally or alternatively, an electronic signal could be digitally sampled and some digital filtering could be performed (e.g., by a processor of the wearable device 110) to generate an extracted ECG waveform. The electronics could include fast recovery circuitry configured to determine that one or more elements (e.g., amplifiers, filters) of the electronics are saturated and to responsively control one or more properties of the electronics (e.g., operate an electronic switch to discharge a capacitor, change a corner frequency or other parameter of a filter) to reduce the electronic saturation of the one or more elements of the electronics. Other configurations and applications of electronics of the wearable device 110 are anticipated.

The wearable device 110 and uses thereof illustrated in FIGS. 1A and 1B are illustrative examples; a wearable device as described herein could be configured in a variety of ways. Generally, such a wearable device could include at least one electrical contact disposed on or toward an inside surface of the wearable device (e.g., on an inside surface of a housing, strap, or other element of the wearable device) such that the at least one electrical contact is in contact with a first external body surface at a first skin location to which the wearable device is mounted. Generally, such a wearable device could also include at least one electrical contact disposed on or toward an outside surface (i.e., an outside contact) of the wearable device (e.g., on an outside surface of a housing, strap, or other element of the wearable device) such that the at least one electrical contact is not in contact with an external body surface at the first skin location to which the wearable device is mounted. The wearable device could be further configured to prevent electrical contact between the outside contact and an external body surface at the first skin location to which the wearable device is mounted, e.g., by increasing a distance between the outside contact and the external body surface, by disposing the outside contact on an outside surface of the wearable device far from an edge of the outside surface, by providing a non-conductive barrier between the outside contact and the external body surface, or operating or configuring the wearable device in some other way.

A wearable device (e.g., 110) could include additional sensors. For example, the wearable device could include accelerometers, optical pulse sensors, photoplethysmographic sensors, pulse oximeters, thermometers, acoustical sensors, force sensors, electric field sensors, magnetic field sensors, or some other sensor(s) configured to detect one or more properties of a wearer of the wearable device and/or of the environment of the wearable device. In some examples, information from different sensors of the wearable device could be combined to determine one or more properties of the wearer (e.g., to determine a health or medical state of the wearer).

For example, a wearable device could be configured to extract an ECG waveform from voltage fluctuations between two or more skin locations of a wearer. The wearable device could be further configured to detect a volume of blood in a portion of subsurface vasculature of the wearer at a plurality of points in time (e.g., by illuminating the portion of subsurface vasculature and detecting light responsively received form the portion of subsurface vasculature, i.e., via photoplethysmography) to generate a waveform of the volume of blood in the portion of subsurface vasculature over time. Time differences or other comparisons of features of the extracted ECG waveform and the determined volume waveform (e.g., a time difference between a maximum of the volume waveform and a corresponding QRS complex of the ECG waveform) could be used to determine a flow rate, a pressure wave speed and/or latency, or other information about the blood in the portion of subsurface vasculature and/or information about the heart and vasculature of the wearer. Further, such determined information could be used to determine a health or medical state of the wearer, e.g., to determine a blood pressure of the wearer, to determine a degree of atherosclerosis of the vasculature of the wearer, etc.

III. Example Wearable Devices

Wearable devices as described herein could be configured in a variety of ways. In some examples, a wearable device could be configured to be mounted to a wrist location of a first arm of the wearer. Further, such a wearable device could include a first electrical contact disposed on a housing (e.g., on an inside surface of the housing) of the wearable device and configured contact skin at wrist location when the wearable device is mounted on the wrist location. Such a wearable device could additionally include a second electrical contact (e.g., disposed on an outside surface of the wearable device) configured to be contacted by skin of a second body surface on a second arm of the wearer such that electronics (e.g., a signal conditioner) of the wearable device could extract an ECG waveform from voltage fluctuations between the first and second electrical contacts when the second electrical contact is contacted by skin of the second body surface and the wearable device is mounted to the wrist location.

Figure 3A:
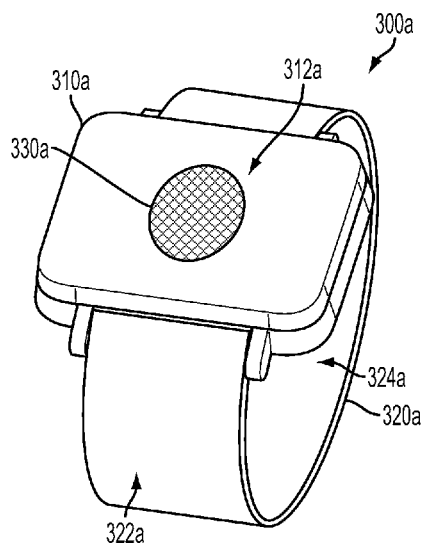
FIG. 3A is a perspective view of an example wearable device.

As an example, FIG. 3A illustrates a wearable device 300a similar to the wearable device 110 illustrated in FIGS. 1A and 1B. The wearable device 300a can be configured to extract an ECG waveform from voltage fluctuations between skin at first and second external body surfaces. The term "wearable device," as used in this disclosure, refers to any device that is capable of being worn at, on or in proximity to an external body surface, such as a wrist, ankle, waist, chest, or other body part. A mount 320a, such as a belt, wristband, ankle band, etc. can be provided to mount the device at, on or in proximity to the external body surface. In some embodiments, a mount could additionally or alternatively include an adhesive. For example, a mount could include an adhesive and could be configured such that it could be used to mount a wearable device to an external body surface of a wearer without wrapping around a part of the wearer (e.g., a limb). The mount 320a may prevent the wearable device 300a from moving relative to the body to ensure consistent contact between an electrical contact or other sensor of the wearable device 300a and the skin to enable consistent extraction of an ECG waveform and/or measurement of some other property of the wearer. In one example, shown in FIG. 3, the mount 320a takes the form of a strap or band that can be worn around a part of the body.

A housing 310a is disposed on the mount 320a such that the housing 310a can be positioned on a first external surface of a first arm of the body (e.g., a surface of a wrist of the body). The housing 310a has an outside surface 312a that is away from the first external surface of the body and an inside surface (not shown) that is toward and/or in contact with the first external surface of the body when the housing 310a is positioned on the first external surface of the body. Similarly, the mount 320a has an inside surface 324a and an outside surface 322a. A second electrical contact 330a is disposed in the middle of the outside surface 312a of the housing 310a and configured to be contacted by skin of a second external body surface of a second arm of the body (i.e., an arm opposite an arm to which the wearable device 300a is mounted). Operated and/or mounted in this way, a first electrical contact (not shown) disposed on the inside surface of the housing 310a could contact skin at the first external surface of the body such that an ECG waveform (as measured between the first and second external body surfaces, e.g., between a wrist of a first arm and a finger of a second, opposite, arm) could be extracted from voltage fluctuations between the first and second 330a electrical contacts.

The first and second 330a electrical contacts could be composed of an electrically conductive material, such as a metal or a combination of metals, or a nonmetal conductor. The first and second 330a electrical contacts could be composed of the same material or different materials. The first and second 330a electrical contacts could each be composed of a single material or could be composed of multiple materials. For example, the electrical contacts could have a bulk composed of a first material and a surface plating of another material. For example, the electrical contacts could have a bulk composed of copper and a surface composed of gold or of gold alloyed with nickel and/or cobalt. Alternatively, the surface layer could be composed of stainless steel, gold, platinum, silver, silver/silver-chloride, polymers or rubbers containing conductive particles, or other conductive or partially conductive materials. The surface layer could be deposited by a number of methods familiar to one skilled in the art; for example, electroplating. Other compositions are possible, as well. Additionally or alternatively, the electrical contacts could be configured to be substantially capacitively coupled to respective external body surfaces by, e.g., including a flat conductor having a substantially nonconductive dielectric coating configured to be in contact with skin. Other compositions and configurations of electrodes are anticipated. Further, protruding aspects of the electrical contacts could have an inscribed, cast, and/or pressed texture or pattern. Additionally or alternatively, the exposed aspects of the electrical contacts could be roughened mechanically, chemically, or by some other method.

One or both of the electrical contacts could be spring loaded. That is, the electrical contacts could be configured to include one or more springs or other elements that could be reversibly compressed. The first electrical contact could be spring loaded in a direction perpendicular to an external surface of the body to which the housing 310a could be mounted. That is, the first electrical contact could be spring loaded in order to improve and/or make more consistent an electrical connection between the first electrical contact and skin of the first external body surface to which the housing 330a is mounted by the mount 320a. Alternatively, the first and/or second 330a electrical contacts could be fixed relative to housing 310a.

The housing 310a could be configured to be water-resistant and/or water-proof. That is, the housing could be configured to include sealants, adhesives, gaskets, welds, press-fitted seams, and/or other joints such that the housing 310a is resistant to water entering an internal volume or volumes of the housing 310a when the housing 310a is exposed to water. The housing 310a could further be water-proof, i.e., resistant to water entering an internal volume or volumes of the housing 310a when the housing 310a is submerged in water. For example, the housing 310a could be water-proof to a depth of 1 meter, i.e., configured to resist water entering an internal volume or volumes of the housing 310a when the housing 310a is submerged to a depth of 1 meter. Further, the interface between the housing 310a and the first and second 330a electrical contacts could be configured such that the combination of the housing 310a and the electrical contacts is water-resistant and/or water-proof.

The wearable device 300a includes electronics (not shown in FIG. 3) electronically coupled to the first and second 330a electrical contacts. The electronics (e.g., electronics configured as a signal conditioner or otherwise as described herein) are configured to extract an ECG waveform from voltage fluctuations between the first and second 330a electrical contacts when the first and second 330a electrical contacts are in contact with respective first and second external surfaces of the body.

The wearable device 300a could be operated based on an ECG waveform extracted as described herein. For example, the wearable device 300a could be configured to determine a health or other state of a wearer based on an extracted ECG waveform. Further, the wearable device 300a could be configured to determine whether the wearable device 300a is mounted to an external body surface of a wearer and/or that an ECG waveform can be extracted using the first and second 330a electrical contacts based on a value, a change in value, and/or some other property of a current and/or voltage detected through and/or between the first and second 330a electrical contacts (e.g., a current and/or voltage detected while a voltage and/or current is being applied, by electronics of the wearable device 300a, through and/or across the first and second 330a electrical contacts).

The electronics or other elements of the wearable device 300a could be configured to prevent injury of a wearer and/or damage to the wearable device 300a due to operation of the device to extract an ECG waveform from voltage fluctuations between two or more external body surfaces using the first and second 330a electrical contacts. Clamping diodes and/or associated blocking resistors could be included in the wearable device 300a and configured to prevent voltages and/or currents above a certain specified maximum from being applied to the electrical contacts (and thus to the skin of the wearer) and/or to elements of the wearable device 300a (e.g., components (e.g., an ADC) of a signal conditioner, components of a recharger coupled to the electrical contacts). A blocking capacitor (i.e., a capacitor having a high specified value of capacitance) could be electrically disposed between one or more or the electrical contacts and electronics of the wearable device 300a to prevent the wearable device 300a from injuring the skin of the external body surface(s) and/or causing electrochemical damage to the electrical contacts (e.g., by preventing the application of direct current to the skin for a protracted period of time, by ensuring that current injected into the skin through the electrical contacts is essentially balanced). Other operations and configurations of the wearable device 300a to prevent injury of a wearer and/or damage to the wearable device 300a are anticipated.

The first and second 330a electrical contacts, and any additional electrical contacts (not shown) protruding from and or disposed on the housing 310a could additionally be used for other purposes. For example, electronics disposed in the wearable device 300a could be used to sense a skin resistance, a skin capacitance, a body water content, a body fat content, a Galvanic skin potential (GSP), an electromyographic (EMG) signal, and/or some other physiological signal present at and/or through the electrical contacts. Additionally or alternatively, the electrical contacts could be used to detect the presence of a charging device or some other electronic system electrically connected to the electrical contacts. The electronics could then use the electrical contacts to receive electrical energy from the charging device or other system to recharge a rechargeable battery of the wearable device 300a and/or to power the wearable device 300a. Such a rechargeable battery could additionally or alternatively be recharged wirelessly using electromagnetic energy received by a coil and other wireless charging circuitry disposed in the wearable device 300a.

Figure 3B:
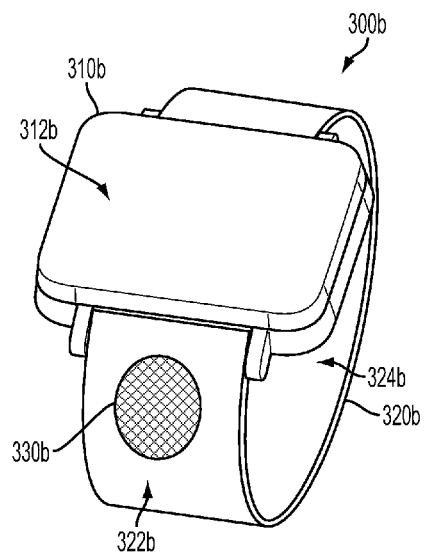
FIG. 3B is a perspective view of an example wearable device.

Alternatively, one or both of the electrical contacts of such a wearable device could be disposed on a band, strap, or other mount of the device. For example, FIG. 3B illustrates a wearable device 300b that can be configured to extract an ECG waveform from voltage fluctuations between skin at first and second external body surfaces. A housing 310b is disposed on a mount 320b such that the housing 310b can be positioned on a first external surface of a first arm of the body (e.g., a surface of a wrist of the body). The housing 310b has an outside surface 312b that is away from the first external surface of the body and an inside surface (not shown) that is toward and/or in contact with the first external surface of the body when the housing 310b is positioned on the first external surface of the body. Similarly, the mount 320b has an inside surface 324b and an outside surface 322b. A second electrical contact 330b is disposed on the outside surface 322b of the mount 320b and configured to be contacted by skin of a second external body surface of a second arm of the body (i.e., an arm opposite an arm to which the wearable device 300b is mounted). Operated and/or mounted in this way, a first electrical contact (not shown) disposed on the inside surface of the housing 310b could contact skin at the first external surface of the body such that an ECG waveform (as measured between the first and second external body surfaces, e.g., between a wrist of a first arm and a finger of a second, opposite, arm) could be extracted from voltage fluctuations between the first and second 330b electrical contacts.

Figure 3C:
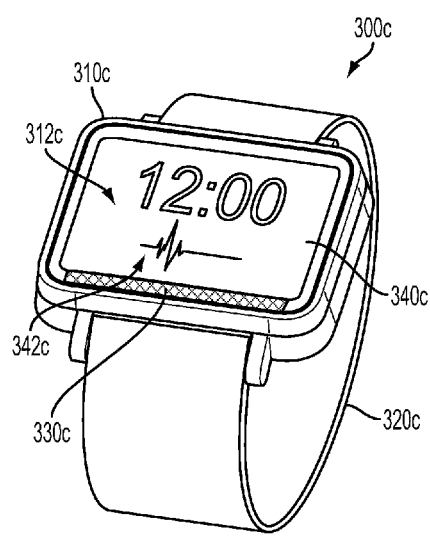
FIG. 3C is a perspective view of an example wearable device.

In some examples, such a wearable device could include a user interface configured to present and/or indicate information to a wearer and/or to receive information (e.g., command inputs) from the wearer. For example, FIG. 3C illustrates a wearable device 300c that can be configured to extract an ECG waveform from voltage fluctuations between skin at first and second external body surfaces. A housing 310c is disposed on a mount 320c such that the housing 310c can be positioned on a first external surface of a first arm of the body (e.g., a surface of a wrist of the body). The housing 310c has an outside surface 312c that is away from the first external surface of the body and an inside surface (not shown) that is toward and/or in contact with the first external surface of the body when the housing 310c is positioned on the first external surface of the body. A first electrical contact (not shown) is disposed on the inside surface of the housing 310c and a second electrical contact 330c is disposed on the outside surface 312c of the housing 310c. Further, the wearable device 300c includes a user interface 340c disposed on the outer surface 312c of the housing.

A wearer of the device 300c may receive one or more recommendations or alerts generated from a remote server or other remote computing device, or from a processor within the device via the user interface 340c. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 340c may be configured and/or operated to provide a visual display 342c to provide an indication of a status of the device, a time, an extracted ECG waveform, or an indication of any other measured physiological parameters measured by the device 300c. Further, the user interface 340c may include one or more buttons and/or be configured as a touch screen for accepting inputs from the wearer. For example, user interface 340*c* may be configured to change the text or other visual information 342*c* in response to the wearer touching one or more locations of the user interface 340*c*.

Figure 3D:
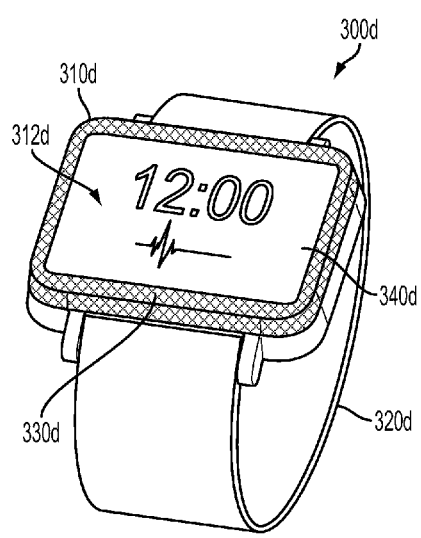
FIG. 3D is a perspective view of an example wearable device.

To allow for easier and/or more comfortable contact between an outward-facing electrode (e.g., 330*a*, 330*b*, 330*c*) and skin of an external body surface of a wearer (e g, skin of a finger, hand, or other part of a wearer's body) and/or according to some other application, the size, shape, number, and/or disposition of such outward-facing electrode(s) could be different than shown above. For example, an outward-facing electrode could partially or completely encircle a band or strap of a wearable device, cover a larger area of an outside surface of a housing (e.g., completely cover such an outside surface), or be configured and/or disposed in some other way. For example, such an outward facing electrode could completely or partially encircle an outer edge of an outside surface of a housing of a wearable device and/or completely or partially encircle a display or other user interface element disposed on such an outside surface. For example, FIG. 3D illustrates a wearable device 300*d* that can be configured to extract an ECG waveform from voltage fluctuations between skin at first and second external body surfaces. A housing 310*d* is disposed on a mount 320*d* such that the housing 310*d* can be positioned on a first external surface of a first arm of the body (e.g., a surface of a wrist of the body). The housing 310*d* has an outside surface 312*d* that is away from the first external surface of the body and an inside surface (not shown) that is toward and/or in contact with the first external surface of the body when the housing 310*d* is positioned on the first external surface of the body. A first electrical contact (not shown) is disposed on the inside surface of the housing 310*d*. A user interface 340*d* is disposed on the outside surface 312*d* of the housing 310*d* A second electrical contact 330*d* is disposed along an edge of the outside surface 312*d* of the housing 310*d* completely enclosing the user interface 340*d*.

Other configurations of a wearable device configured to extract an EG waveform from two or more skin locations of the body of a wearer are anticipated. Such wearable devices could include more than two electrodes configured to provide additional information to extract additional ECG waveforms, to extract higher-quality (e.g., higher-magnitude, higher signal-to-noise-ratio) ECG waveforms, to detect some other information (e.g., to detect a skin resistance, to detect a Galvanic skin response, to detect an EMG signal (e.g., an EMG signal from muscles in a wrist of a wearer), or to enable some other application. In some examples, an electrical contact could additionally be configured to detect contact with skin (e.g., a finger) of the wearer and the wearable device could operate responsive to such a detection, e.g., to extract an ECG waveform from voltage fluctuations between the electrical contact and some other electrical contact(s). Additionally or alternatively, touch detection by an electrical contact could be used to receive an input from the wearer, e.g., to act as a 'button press' or other indication of a wearer's intent. Further, a wearable device could include multiple such electrical contacts configured to detect skin contact (e.g., to initiate an ECG waveform extraction, to determine user input) and to enable ECG waveform extraction. Additionally or alternatively, such an electrode could form a transparent or semi-transparent layer disposed on a display of the wearable device. For example, a layer of indium-tin-oxide, an array of fine wires or other conductive elements, or some other elements could be disposed on a display and configured to act as an electrical contact. Additionally or alternatively, an electrode of a touchscreen could be configured to capacitively couple with voltage fluctuations of a skin location of a wearer such that an ECG waveform could be extracted from voltage fluctuations between the touchscreen electrode and some other electrical contact(s) of the wearable device.

In some examples, the wearable device (e.g., a housing 310*a*, 310*b*, 310*c*, 310*d* of the wearable device 300*a*, 300*b*, 300*c*, 300*d*) further includes at least one detector for detecting at least one other physiological parameter, which could include any parameters that may relate to the health of the person wearing the wearable device and/or the environment of the wearable device. For example, the detector could be configured to measure acceleration of the wearable device, a magnetic field, an electric field, an ambient light, a respiration rate, a skin temperature, etc. At least one of the detectors could be configured to non-invasively measure a volume of blood circulating in subsurface vasculature proximate to the wearable device. In a non-exhaustive list, the detector may include any one of an optical (e.g., CMOS, CCD, photodiode), acoustic (e.g., piezoelectric, piezoceramic), electrochemical (voltage, impedance), thermal, mechanical (e.g., pressure, strain, acceleration, rotation), magnetic, or electromagnetic (e.g., RF, magnetic resonance) sensor.

For example, a wearable device could be configured to extract an ECG waveform from voltage fluctuations between two or more skin locations of a wearer. The wearable device could be further configured to detect a volume of blood in a portion of subsurface vasculature of the wearer at a plurality of points in time (e.g., by illuminating the portion of subsurface vasculature and detecting light responsively received form the portion of subsurface vasculature, i.e., via photoplethysmography) to generate a waveform of the volume of blood in the portion of subsurface vasculature over time (e.g., a photoplethysmographic signal). Time differences or other comparisons of features of the extracted ECG waveform and the determined volume waveform (e.g., a time difference between a maximum of the volume waveform and a corresponding QRS complex of the ECG waveform) could be used to determine a flow rate, a pressure wave speed and/or latency, or other information about the blood in the portion of subsurface vasculature and/or information about the heart and vasculature of the wearer. Further, such determined information could be used to determine a health or medical state of the wearer, e.g., to determine a blood pressure of the wearer, to determine a degree of atherosclerosis of the vasculature of the wearer, etc.

Further, a wearable device as described herein could be modular. That is, one or more components of such a wearable device could be replaceable, extensible, and/or otherwise reconfigurable to add and/or remove capabilities of the wearable device. For example, a wearable device could include a housing containing a battery, a communications interface, a touchscreen user interface, and general-purpose electronics to enable a variety of applications of a wearable device. The wearable device could further include a modular mount configured to mount the housing to an external body surface and to enable some applications of the wearable device, e.g., by including one or more sensors. For example, a first modular mount could be configured to mount the housing around a wrist of a wearer and to enable extraction of an ECG waveform from voltage fluctuations between the arms of a wearer by providing a second electrical contact on an outside surface of the mount (e.g., an outer surface of a frame encircling the housing) to complement a first electrical contact provided by the housing on an inside surface of the housing. A second modular mount could be configured to mount the housing around the chest of a wearer and to enable detection of breathing patterns of the wearer by providing a strain sensor in a band of the mount that encircles the chest of the wearer.

Figure 4A:
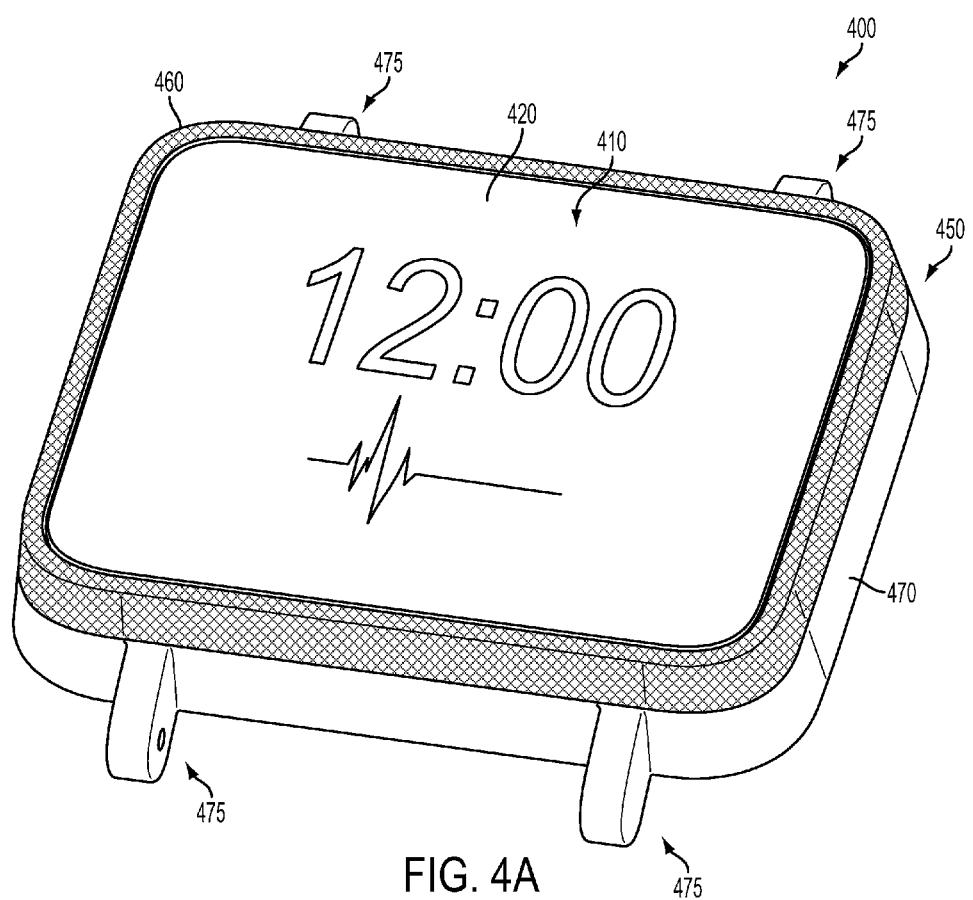
FIG. 4A is a top perspective view of elements of an example wearable device.

FIG. 4A illustrates a top perspective view of an example wearable device 400 including a central housing 410 configured to be removably seated in a frame 450 of a modular mount. The modular mount additionally includes a band (not shown) connected to the frame 450 and configured to mount the central housing 410 to an external body surface (e.g., a wrist) of a wearer. The central housing 410 includes a user interface 420 disposed on an outer surface of the central housing 410 (e.g., a surface opposite the external body surface when the central housing 410 is mounted to the external body surface by the modular mount). The user interface 420 is a touchscreen interface, configured to present visual indications to a wearer (e.g., by spatially modulating an emitted light of the user interface 420 and/or by spatially modulating a reflectivity of the user interface 420). The frame 450 includes a nonconductive inner portion 470 and a conductive outer portion 460. The outer portion 460 is configured to act as an electrical contact and to contact skin of an external body surface of the wearer (e.g., skin of a finger of the wearer). The outer portion 460 encircles the user interface 420 when the central housing 410 is seated in the frame 450 (as shown in FIG. 4A). The inner portion 470 of the frame 450 includes mounting points 475 configured to attach a band, strap, or other means of securing the wearable device 400 to an external body surface (e.g., the mounting points 475 could be configured to attach to a standard watch band, i.e., they could be approximately 26 millimeters apart, 20 millimeters apart, or some other distance apart according to a stand watch band size).

Figure 4B:
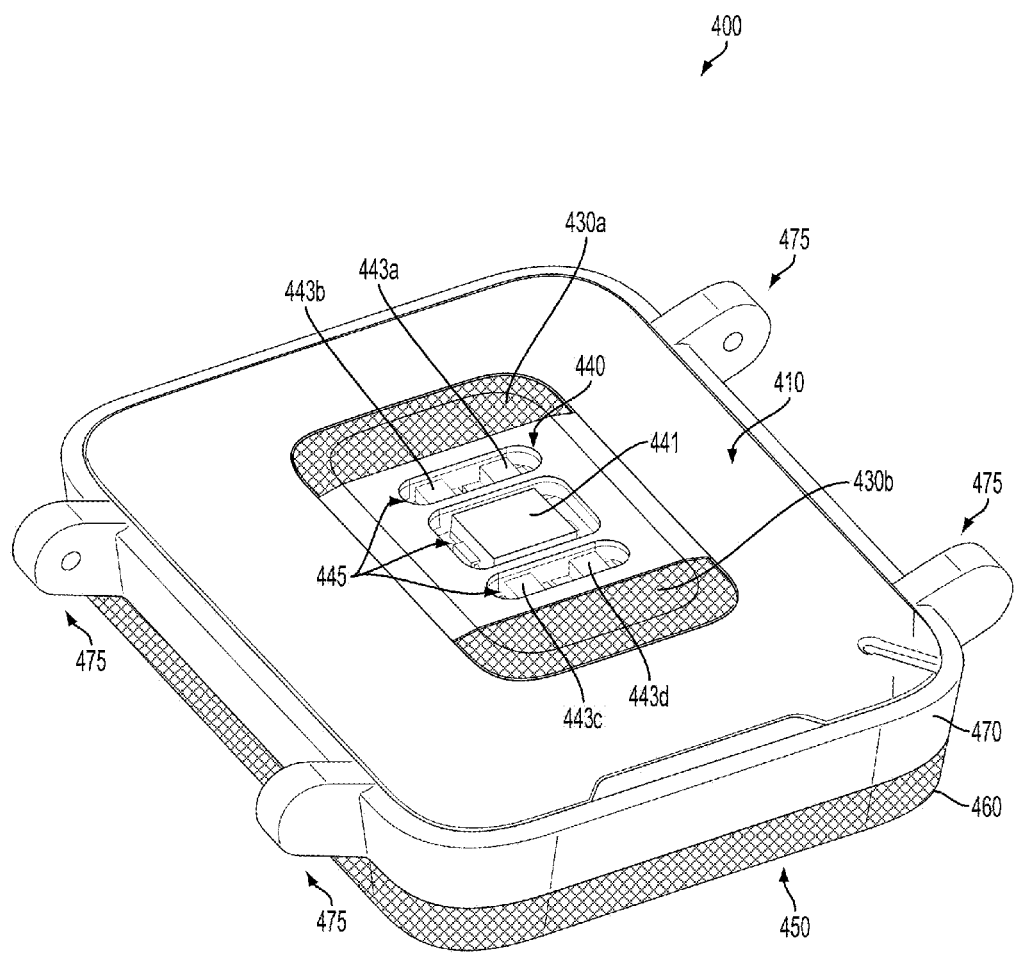
FIG. 4B is a bottom perspective view of the elements of the example wearable device illustrated in FIG. 4A.

FIG. 4B illustrates a bottom perspective view of the wearable device 400 illustrating elements disposed on an inside surface of the central housing 410 (i.e., elements disposed toward the external body surface when the central housing 410 is mounted to the external body surface by the modular mount). Electrical contacts 430a, 430b are disposed on the inside surface of the central housing 410. The electrical contacts 430a, 430b could be configured to enable a variety of applications of the wearable device 400. For example, the electrical contacts 430a, 430b could be operated to detect a skin resistance, a skin capacitance, a Galvanic skin response, a body water content, a body fat content, or other information by passing a current through and/or applying a voltage to skin proximate to the wearable device and detecting a corresponding voltage across and/or current through the electrical contacts 430a, 430b. Further, a Galvanic skin voltage, an EMG waveform, or some other electrophysiological voltage signal could be detected through the electrical contacts 430a, 430b. In some examples, an electro-haptic stimulus could be delivered to a wearer though the electrical contacts 430a, 430b. In some examples, a temperature sensor could be thermally coupled to one or more of the electrical contacts 430a, 430b to enable the detection of the temperature of skin proximate to the one or more electrical contacts 430a, 430b.

Further, an ECG waveform could be extracted from voltage fluctuations between the outer portion 460 of the frame and one or more electrical contacts 430a, 430b when the central housing 410 is mounted to a first external body surface (e.g., skin of a wrist of a first arm of a wearer) and a second body surface (e.g., skin of a finger of an arm of the wearer opposite the arm to which the wearable device is mounted) is in contact with the outer portion 460 of the frame 450. Other operation of the wearable device 400 to extract and ECG signal of a wearer, as described herein or otherwise, are anticipated.

In some examples, the outer portion 460 of the frame and one or more electrical contacts 430a, 430b could be composed of similar materials and/or configured to couple to voltage fluctuations of skin similarly. For example, the outer portion 460 of the frame and one or more electrical contacts 430a, 430b could all have surfaces composed of silver/silver-chloride and could make ohmic electrical contact with skin. In another example, the outer portion 460 of the frame and one or more electrical contacts 430a, 430b could all have surfaces composed of a substantially non-conductive dielectric and could make substantially capacitive electrical contact with skin. Further, the outer portion 460 of the frame and one or more electrical contacts 430a, 430b could be composed of different materials and/or configured to couple to voltage fluctuations of skin differently. For example, the outer portion 460 of the frame could have surfaces composed of silver/silver-chloride and could make ohmic electrical contact with skin, while the electrical contacts 430a, 430b could have surfaces composed of a substantially non-conductive dielectric and could make substantially capacitive electrical contact with skin. Other combinations of electrode configurations and compositions are anticipated.

The central housing 410 additionally includes an optical sensor 440. The optical sensor 440 includes a photodetector 441 and four light sources 443a, 443b, 443c, 443d. The photodetector 441 and light sources 443a, 443b, 443c, 443d are disposed behind protective windows 445. The four light sources 443a, 443b, 443c, 443d could be similarly or differently configured. The photodetector could be any element configured to electronically detect one or more properties (e.g., wavelength, spectral profile, amplitude, amplitude within a specified range of wavelengths) of received light (e.g., a photodiode, a phototransistor, a photoresistor, an avalanche photodiode). The four light sources 443a, 443b, 443c, 443d could include LEDs, laser, or other elements configured to emit light. Further, the four light sources 443a, 443b, 443c, 443d could be configured to emit light having one or more specified properties (e.g., a specified wavelength, a specified amplitude, a specified waveform over time, a specified pulse or other timing). The optical sensor 440 could be configured to illuminate target tissues (e.g., using the light sources 443a, 443b, 443c, 443d) and to detect light responsively or otherwise emitted from the target tissue (e.g., using the photodetector 441) to detect one or more properties of the target tissue.

Figure 4C:
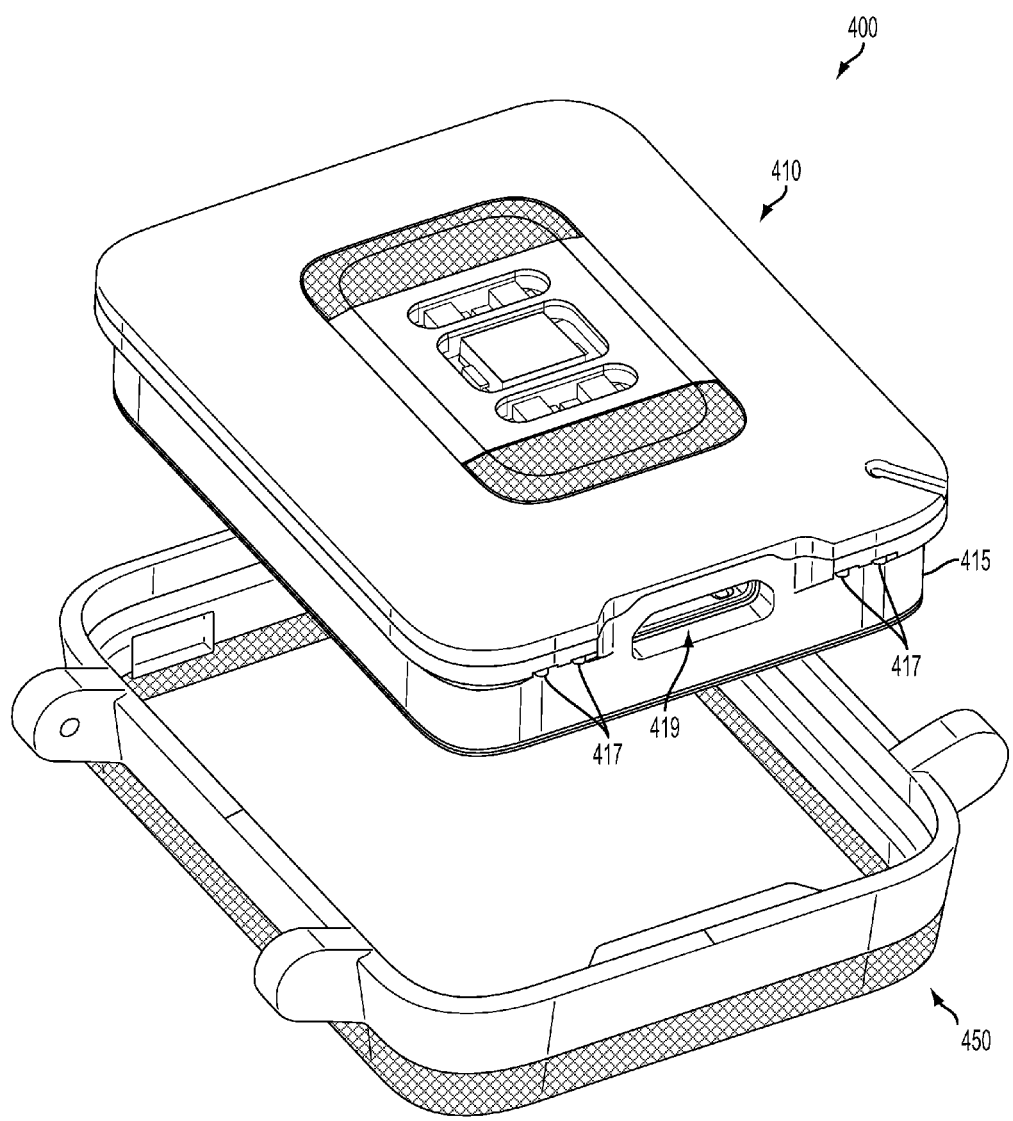
FIG. 4C is a bottom perspective view of the elements of the example wearable device illustrated in FIG. 4A, when a housing and a frame of the elements are disengaged from each other.
Figure 4D:
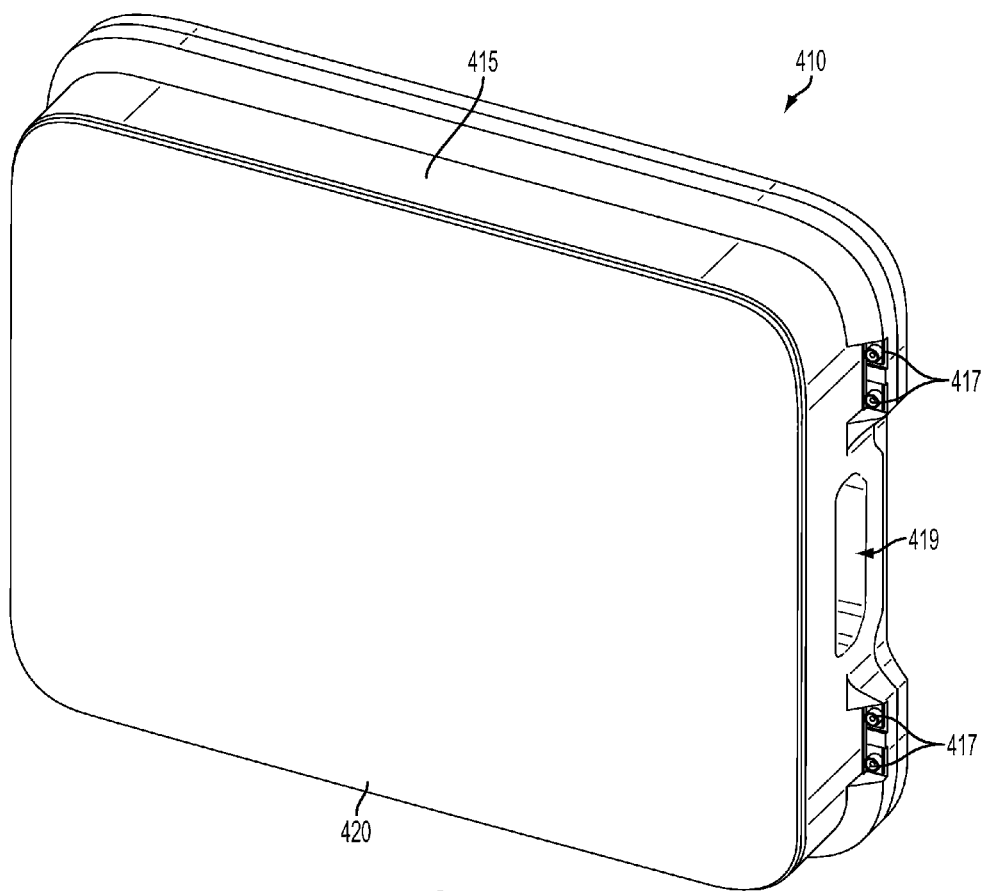
FIG. 4D is a top perspective view of the housing of the elements of the example wearable device illustrated in FIG. 4A.

FIG. 4C illustrates a bottom perspective view of the wearable device 400 when the central housing 410 has been unseated from the frame 450. FIG. 4C illustrates a nonconductive housing 415, a wired interface 419, and contact pads 417 of the central housing. The wired interface 419 could be any interface configured to receive one or more conductors configured, e.g., as a connector such that power and electronic signals may be transmitted to and/or received from electronics disposed in the central housing 410. For example, the wired interface 419 could be a micro-USB interface. The contact pads 417 are configured to allow electrical contacts between electronics of the central housing 410 and electronics or other elements of a modular frame (e.g., the conductive electrical contact formed by the outer portion 460 of the frame 450). These elements are further illustrated by FIG. 4D, which illustrates a top perspective view of the central housing 410.

Note that the contact pads 417 could be electrically connected within the central housing 410 or could be electrically independent. That is, the contact pads 417 could be electrically connected together such that the contact pads 417 cannot be used to transfer different electrical signals. Alternatively, the contact pads 417 could be electrically distinct (e.g., could be connected to separate components of electronics within the central housing 410) and thus could be used to transfer different electrical signals. For example, the four contact pads 417 could be connected to respective four distinct electrical contacts or electrodes of a modular frame into which the central housing 410 could be removably seated. Additionally or alternatively, a modular frame could electrically connect one or more of the four contact pads 417 together according to some application. For example, a first contact pad could be configured to detect a voltage, a second contact pad could be configured to source and/or sink a specified current, and the modular frame could connect the first and second contact pads to a single electrical contact to enable the determination of a resistance of some target (e.g., of a portion of skin, by determining a voltage across the portion of skin related to the specified current injected into the portion of skin) In some applications, two of the contact pads 417 could be configured to provide power to a component of the modular mount, and the remaining two contact pads 417 could be configured to transmit and/or received data to/from elements of the modular mount (e.g., an active sensor of the modular mount). Additionally or alternatively, such a configuration of the contact pads 417 could be used to facilitate communication between the central housing 410 and some other system, e.g., to facilitate reprogramming of electronics of the central housing 410, to facilitate data transfer of logged data stored in a data storage of the central housing, or some other application. Additional or alternative configurations and applications of the contact pads 417 and of the central housing 410 are anticipated.

Figure 4E:
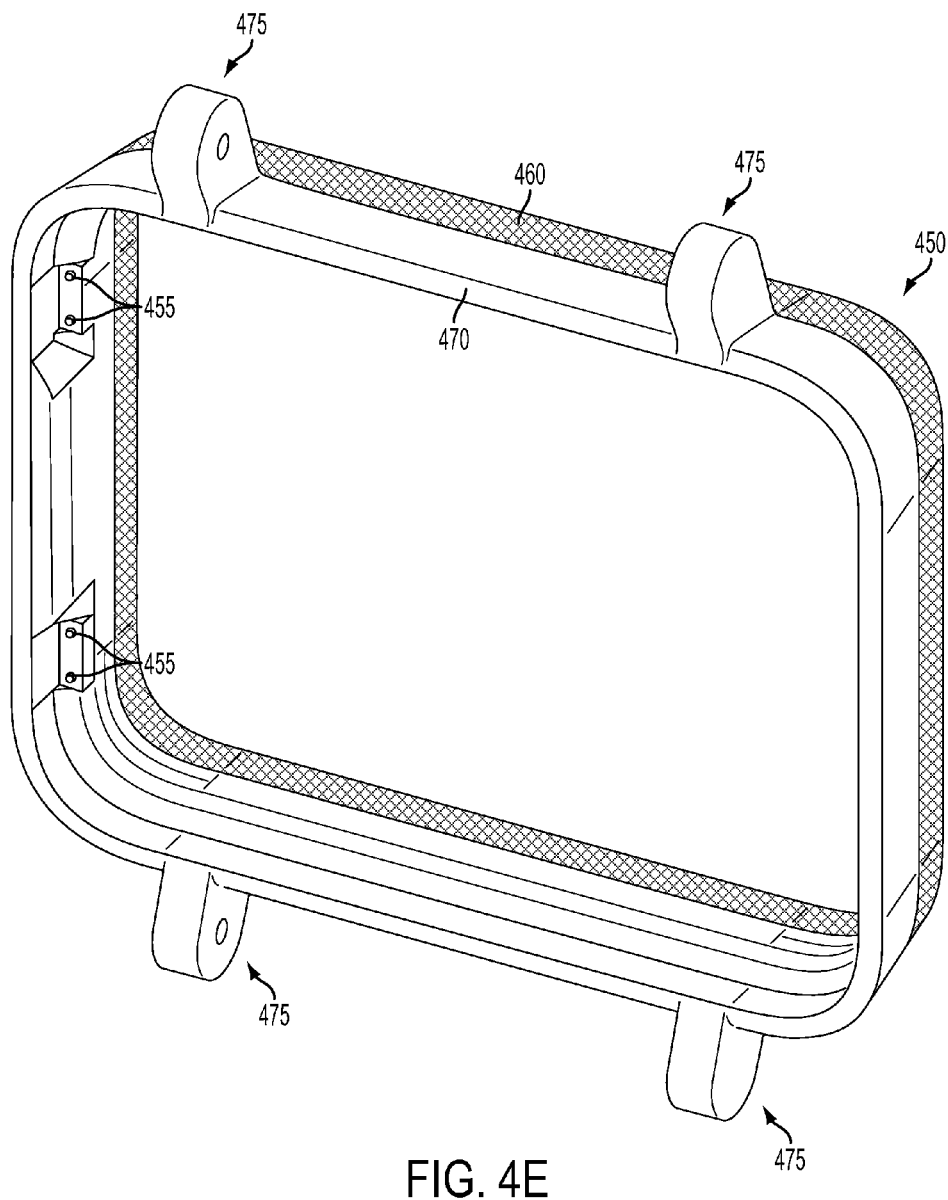
FIG. 4E is a bottom perspective view of the frame of the elements of the example wearable device illustrated in FIG. 4A.
Figure 4F:
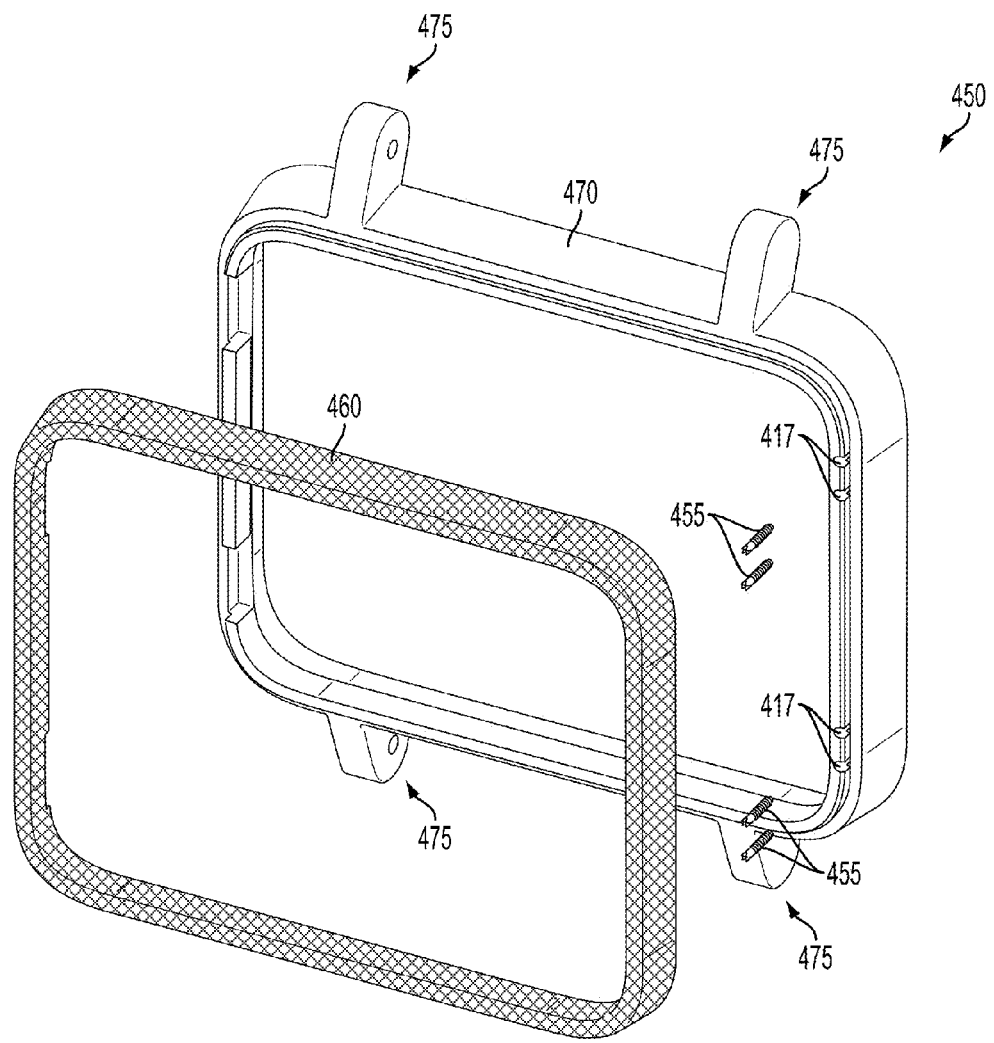
FIG. 4F is an exploded top perspective view of the frame of the elements of the example wearable device illustrated in FIG. 4A.

FIGS. 4E and 4F show bottom perspective and top perspective exploded views of the frame 450, respectively. The frame 450 includes four spring-loaded contacts 455 configured to maintain electrical contact between the outer portion 460 of the frame 450 and the contact pads 417 of the central housing 410 when the central housing 410 is seated in the frame 450. The spring-loaded contacts 455 are disposed within and retained by respective holes 475 formed in the inner portion 470 of the frame 450. Note that some or all of the spring-loaded contacts 455 could alternatively be disposed as part of the central housing 410. Further all of the spring-loaded contacts 455 are in electrical contact with each other and with the outer portion 460 (i.e., the electrical contact) of the frame 450, but individual contacts of the spring-loaded contacts 455 could be in electrical contact with electrically distinct elements (e.g., separate electrical contacts, some other electrical and/or electronic element(s)) of a modular frame.

FIG. 5 is a simplified schematic of a system 500 including one or more wearable devices 510. The one or more wearable devices 510 may be configured to transmit data via a communication interface 515 over one or more communication networks 520 to a remote server 530. In one embodiment, the communication interface 515 includes a wireless transceiver for sending and receiving communications (e.g., indications of a measured skin resistance and/or capacitance) to and from the server 530. In further embodiments, the communication interface 515 may include any means for the transfer of data, including both wired and wireless communications. For example, the communication interface 515 may include a universal serial bus (USB) interface or a secure digital (SD) card interface. Communication networks 520 may include any of: a plain old telephone service (POTS) network, a cellular network, a fiber network and a data network. The server 530 may include any type of remote computing device or remote cloud computing network. Further, communication network 520 may include one or more intermediaries, including, for example wherein the wearable device 510 transmits data to a mobile phone or other personal computing device, which in turn transmits the data to the server 530.

In addition to receiving communications from the wearable device 510, such as data regarding health and/or affect state as input by the user or extracted electrocardiographic (ECG) waveforms, the server may also be configured to gather and/or receive either from the wearable device 510 or from some other source, information regarding a wearer's overall medical history, environmental factors and geographical data. For example, a user account may be established on the server for every wearer that contains the wearer's medical history. Moreover, in some examples, the server 530 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. If measuring physiological parameters of the user (e.g., extracted ECG waveforms), such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

Further, some embodiments of the system may include privacy controls which may be automatically implemented or controlled by the wearer of the device. For example, where a wearer's collected data are uploaded to a cloud computing network for analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

IV. Example Electronics Disposed in a Wearable Device

Figure 6:
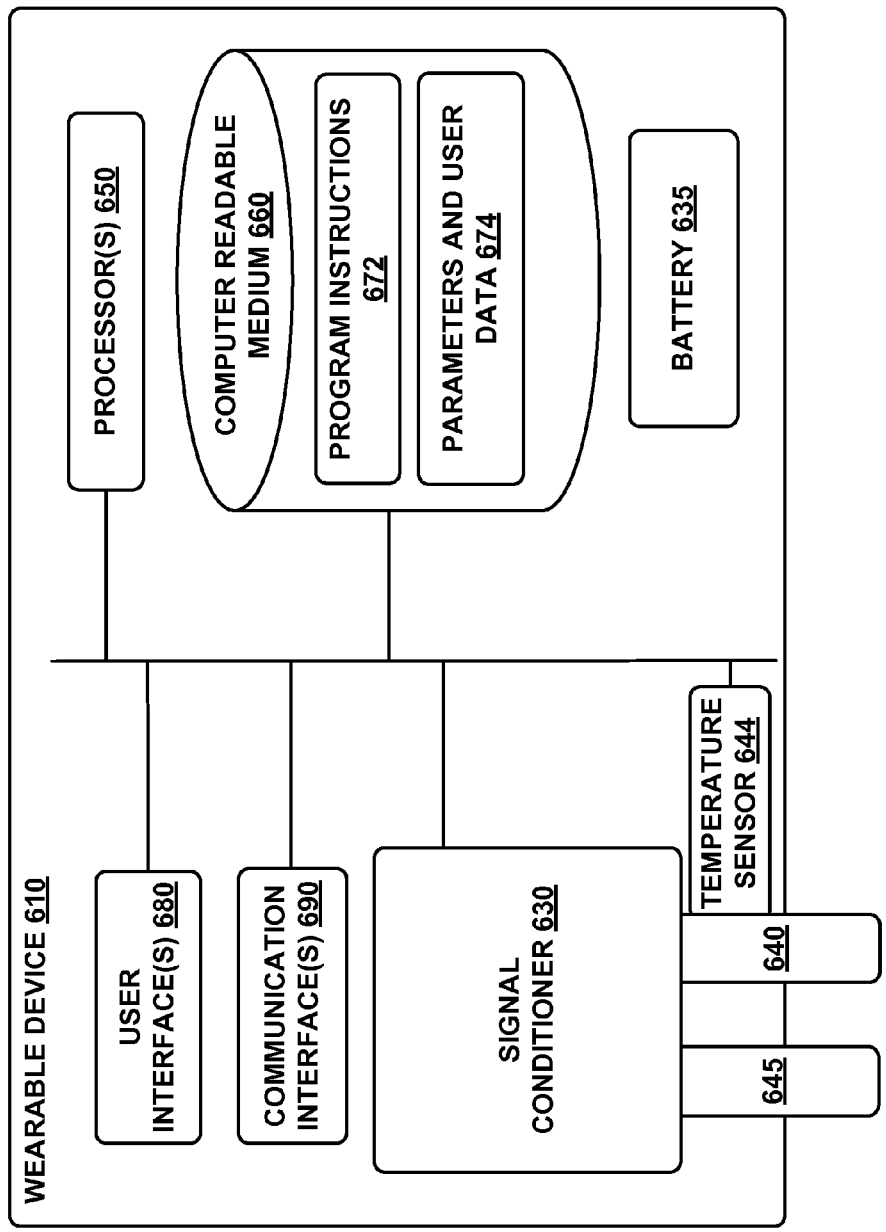
FIG. 6 is a functional block diagram of components disposed in an example wearable device.

FIG. 6 is a simplified block diagram illustrating the components of a wearable device 600, according to an example embodiment. Wearable device 600 may take the form of or be similar to one of wearable device 110, 210, 300a, 300b, 300c, 300d, and 400 shown in FIGS. 1A-B, 2, 3A-D, and 4A-4F. However, wearable device 600 may also take other forms, for example, an ankle, waist, or chest-mounted device.

In particular, FIG. 6 shows an example of a wearable device 610 having a signal conditioner 330 for extracting an electrocardiographic (ECG) waveform from voltage fluctuations between two skin locations proximate to the wearable device 610, a rechargeable battery 635, a user interface 680, communication interface 690 for transmitting data to a server, a temperature sensor 644, and processor(s) 650. The components of the wearable device 600 may be disposed on or within a mount and/or housing for mounting the wearable device and components thereof to an external body surface, e.g., one of the two skin locations from which the signal conditioner 330 is configured to extract an ECG waveform. The wearable device 610 also includes a first electrical contact 640 and a second electrical contact 645 operatively coupled to the signal conditioner 630. The signal conditioner 630 uses the first and second electrical contacts 640, 645 to extract an ECG waveform from voltage fluctuations between first and second skin locations proximate to respective first and second electrical contacts 640, 645. The signal conditioner 630 could be configured to perform other functions using the first and second electrical contacts 640, 645 and/or further electrical contacts of the wearable device 600. For example, the signal conditioner 630 could be configured to interface with a charger or other external device or system to power the electronics and to recharge the rechargeable battery 635, to determine that the first and second electrical contacts 640, 645 are in contact with skin and/or that an ECG waveform can be extracted from voltage fluctuations between them 640, 645, to determine a skin resistance and/or capacitance between the electrical contacts 640, 645 and/or some other electrical contacts, or some other function (s). Additionally or alternatively, the rechargeable battery 635 could be charged wirelessly using a coil and/or other components of the wearable device 600 (not shown). Additionally, the temperature sensor 644 is thermally coupled to the first electrical contact 640 such that the temperature sensor 644 can be used to obtain a measurement related to the temperature of skin proximate to the first electrical contact 640.

Processor 650 may be a general-purpose processor or a special purpose processor (e.g., digital signal processors, application specific integrated circuits, etc.). The one or more processors 650 can be configured to execute computer-readable program instructions 672 that are stored in a computer readable medium 660 (i.e., data storage) and are executable to provide the functionality of a wearable device 600 described herein.

The computer readable medium 660 may include or take the form of one or more non-transitory, computer-readable data storage media that can be read or accessed by at least one processor 650. The one or more computer-readable storage media can include volatile and/or non-volatile storage components, such as optical, magnetic, organic or other memory or disc storage, which can be integrated in whole or in part with at least one of the one or more processors 650. In some embodiments, the computer readable medium 660 can be implemented using a single physical device (e.g., one optical, magnetic, organic or other memory or disc storage unit), while in other embodiments, the computer readable medium 660 can be implemented using two or more physical devices.

The signal conditioner 630 could include a variety of components configured in a variety of ways to allow one or more ECG waveforms to be extracted from voltage fluctuations between the electrical contacts 640, 645 when the electrical contacts 640, 645 are contacting appropriate respective skin locations of a wearer and/or to allow other operations and applications. The signal conditioner 630 could include analog and/or digital electronic components to enable analog and/or digital manipulations of electrical signals related to voltage fluctuations between the electrical contacts 640, 645. In some examples, the signal conditioner 630 could include one or more analog electronic components (e.g., amplifiers, transistors, op-amps, analog filters) assembled into an analog front-end and configured to amplify, buffer, filter, or otherwise act on voltage fluctuations between the electrical contacts 640, 645 and to present one or more analog electronic outputs to digital components of the signal conditioner 630 and/or other elements of the wearable device 600 (e.g., to an ADC or other component of the processor 650).

Generally, the signal conditioner 630 includes components configured to amplify and filter voltage fluctuations between the electrical contacts 640, 645. The signal conditioner 630 could include one or more amplifiers, buffers, filters, operational amplifiers, resistors, capacitors, inductors, transistors, rectifiers, or some other linear or nonlinear electronic component or combinations thereof. Such components could be formed as a number of discrete signal processing blocks (e.g., discrete sets of components configured to perform some operation(s) on electronic input(s) to form electronic output(s)) that are connected together (e.g., the output(s) of a first block form the input(s) of one or more other blocks).

In some embodiments, the signal conditioner 630 could be configured to generate an electronic signal (e.g., to generate an extracted ECG waveform) that is related to a band-passed version of the voltage fluctuations between the electrical contacts 640, 645. This could include applying the voltage fluctuations to a band-pass filter having a pass-band between approximately 0.05 Hertz and approximately 150 Hertz. The signal conditioner 630 could additionally apply a notch filter (at, e.g., approximately 60 Hertz) to remove some narrow-band signal from the voltage fluctuations (e.g., to remove approximately 60 Hertz noise emitted by power mains in the environment of the wearable device 600). Additionally or alternatively, an electronic signal could be digitally sampled and some digital filtering could be performed (e.g., by the processor 650) to generate an extracted ECG waveform. In such examples, the processor 650 and elements thereof (e.g., an ADC of the processor) could be considered part of an overall signal conditioner configured to extract an ECG waveform from voltage fluctuations between the electrical contacts 640, 645.

The signal conditioner 630 could include a fast response circuit or other circuitry or components configured to allow the signal conditioner 630 to extract an ECG waveform after the voltage fluctuations between the electrical contacts 640, 645 exhibit a large change (e.g., a change in baseline voltage level, a spike or other transient related to an electrostatic discharge, a skin location coming into contact with one of the electrical contacts, and/or a skin location moving relative to one or both of the electrical contacts 640, 645). For example, the signal conditioner 630 could be configured to determine that one or more elements (e.g., amplifiers, op-amps, signal processing blocks) of the signal conditioner 630 are electronically saturated (i.e., outputting a maximal and/or minimal signal level, or having an internal signal that has a maximal or minimal value) and to responsively control one or more properties of the signal conditioner 630 to reduce the electronic saturation of the one or more elements of the signal conditioner 630.

Determining that one or more elements of the signal conditioner are electronically saturated could include sampling an output or other electronic signal of the signal conditioner 630 using an ADC and making a determination related to one or more digital outputs of the ADC, applying an output or other electronic signal of the signal conditioner 630 to a comparator, Schmitt trigger, or other digital component, or some other determination. Further, controlling one or more properties of the signal conditioner 630 to reduce the electronic saturation of the one or more elements of the signal conditioner 630 could include discharging a capacitor, switching in and/or out one or more signal-processing blocks of the signal conditioner 630, and/or changing a corner frequency, pass-band, or other parameter(s) of a filter (e.g., increasing a corner frequency of a high-pass filter to allow the output of the filter to more quickly reduce from a saturation level). These methods of control could be implemented by operating one or more electronic switches, transistors, or other elements.

Additionally or alternatively, fast response or other circuitry of the signal conditioner 630 could prevent electronic saturation of one or more elements of the signal conditioner 630 by having a nonlinear property; for example, a metal-oxide varistor or other electronic elements or combinations thereof having a nonlinear current-voltage characteristic (e.g., having a lower resistance and/or impedance at higher voltages than at lower voltages) could be included in the signal conditioner 630 (e.g., could be connected across a filtering or other capacitor, could be connected between a signal line and a ground plane). Fast response or other circuitry of the signal conditioner 630 configured to prevent electronic saturation of one or more elements of the signal conditioner 630 could exhibit hysteresis. For example, fast response circuitry could include a Schmitt trigger configured to close a capacitor-discharging switch when the voltage across the capacitor exceeds a first specified level and to subsequently open the capacitor-discharging switch when the voltage across the capacitor falls below a second specified level.

The signal conditioner 630 could include circuitry or other elements configured to detect and/or determine whether the first and second electrical contacts 640, 645 are in contact with skin and/or that an ECG waveform can be extracted from voltage fluctuations between them 640, 645. The signal conditioner 630 could include circuitry (e.g., voltage dividers, relaxation oscillators, current injectors) configured to actively or passively detect an effective resistance and/or capacitance between the first and second electrical contacts 640, 645 that could be used to determine that the first and second electrical contacts 640, 645 are in contact with skin and/or that an ECG waveform can be extracted therefrom. Such circuitry could additionally be configured and/or operated to detect other properties of a wearer, e.g., a body water content, a body fat content. Additionally or alternatively, the signal conditioner 630 could include circuitry (e.g., comparators, Schmitt triggers, overvoltage sensors, differentiators, fast response circuitry) configured to detect electrostatic discharges, voltage transients, changes in voltage offsets, or other properties of voltage fluctuations between the first and second electrical contacts 640, 645 that are related to the electrical contacts 640, 645 coming into and/or leaving contact with skin of a wearer.

A voltage sensor of the signal conditioner 630 (and/or of the processor 650) could include one or more comparators, Schmitt triggers, direct-conversion ADCs, successive-approximation ADCs, sigma-delta ADCs, or some other type(s) of ADC. The voltage sensor could include an amplifier, a filter, a sample-and-hold, and/or some other components. Further, individual elements of the signal conditioner 630 could be embodied as respective discrete components. Additionally or alternatively, one or more elements of the signal conditioner 630 could be incorporated into one or more integrated circuits (e.g., an integrated circuit that includes elements of the processor 650, the communication interface(s) 690, and/or elements of the wearable device 600. In examples where the signal conditioner 630 are included in a wearable device composed of multiple housings or other subassemblies, the elements of the signal conditioner 630 could all be disposed in a single housing or subassembly or elements of the signal conditioner 630 could be disposed in multiple housings or subassemblies and connected using wires, cables, or other means passing between housings or subassemblies.

In some examples, voltage sources, electronic switches, amplifiers, filters, op-amps, voltage sensors (e.g., ADCs, comparators, Schmitt triggers), and/or other elements of the signal conditioner 630 could be elements of a microprocessor (e.g., of 650) that are electronically coupled to a pin of the microprocessor (e.g., logic gates, capacitors, high-impedance electrical switches (e.g., CMOS FETs), or other microelectronics). For example, a voltage source of the signal conditioner 630 could be an internal voltage supply of the microprocessor, and a voltage source switch of the signal conditioner 630 could be a gate of the microprocessor configured to electrically connect the internal voltage supply and/or an internal ground of the microprocessor to a pin of the microprocessor and to appear as a high impedance element when not connecting the pin to the internal voltage supply and/or the internal ground (e.g., to provide a 'three-state' digital output to the pin). An ADC of the microprocessor could additionally be configured to electrically connect to the pin and to act as a voltage sensor of the signal conditioner 630.

In some examples, the signal conditioner 630 could include circuitry to protect elements of the wearable device 600 (e.g., to protect amplifiers, filters, voltage sensors, or other elements of the signal conditioner 630) from high voltages and/or currents present across and/or through the electrical contacts 640, 645. For example, the signal conditioner 630 could include clamping diodes, blocking resistors, blocking capacitors, electronic switches, or other elements configured to prevent components of the signal conditioner 630 from being damaged by voltages and/or currents at/through the electrical contacts 640, 645. These elements of the signal conditioner 630 could be configured to protect the wearable device 600 from electrostatic discharges from the environment of the wearable device 600.

The signal conditioner 630 could include additional components. In some examples, the signal conditioner 630 could include a recharger configured to recharge the rechargeable battery 635 and to be powered through the electrical contacts 640, 645 and/or some additional electrical contact(s). In some examples, the wearable device 600 could be configured to be mounted on an external charger. The external charger could be configured to apply a voltage and/or current to the electrical contacts (e.g., 640, 645) sufficient to power the recharger to recharge the rechargeable battery 635. The signal conditioner 630 could include rectifiers, capacitors, or other elements disposed electrically between the recharger and the electrical contacts (e.g., 640, 645). The rectifiers or other elements could be configured to reduce electrical interference in ECG waveform measurements made using the electrical contacts 640, 645 when the wearable device 600 is mounted to an external surface of a wearer and not mounted to an external charger. Additionally or alternatively, the wearable device 600 could include a coil and other components configured to receive electromagnetic energy (e.g., from a wireless charger) and to recharge the rechargeable battery 635 using the received electromagnetic energy. The signal conditioner 630 could include components configured to detect an EMG, a skin resistance, a skin capacitance, a body water content, a body fat content, a Galvanic skin response, or some other electrical signal using the electrical contacts 640, 645 and/or some additional electrical contact(s). The signal conditioner 630 could include components to operate some other sensors (e.g., accelerometers, optical pulse sensors, photoplethysmographic sensors, pulse oximeters, thermometers, the temperature sensor 644) configured to detect one or more properties of a wearer of the wearable device 600 and/or of the environment of the wearable device 600.

Note that, while the signal conditioner 630, processor(s) 650, rechargeable battery 635, and other components are sometimes described herein as being disposed on or within a single housing, other configurations are anticipated. In some examples, a wearable device could include multiple housings, and the components of the wearable device 600 could be distributed amongst the multiple housings. For example, a first housing could contain some elements of the signal conditioner 630 (for example, ECG waveform extraction electronics, temperature sensing electronics) and the electrical contacts 640, 645 could protrude from the first housing. A second housing could include the recharger electronics and the rechargeable battery 635 and elements disposed in the second housing could be electrically connected to elements disposed in the first housing. In some examples, the wearable device 600 could include a modular mount and a housing configured to be removably seated in a frame of the modular mount. The first electrical contact 640, elements of the signal conditioner 630, and/or other elements of the wearable device 600 (e.g., 650, 660, 680, 690, 635) could be disposed on or within the housing. The second electrical contact 645 (and other elements) could be disposed on or within the modular mount (e.g., on an outside surface of the frame, on an outside surface of a band of the modular mount) and maintained in electrical contact with elements of the housing (e.g., 630) via spring-loaded contact(s) or some other means. Other numbers of housings, configurations of housings, and dispositions of components within multiple housings are anticipated.

The program instructions 672 stored on the computer readable medium 660 may include instructions to perform or facilitate some or all of the device functionality described herein. For instance, program instructions 672 could include instructions to operate the signal conditioner 630 to extract an ECG waveform from voltage fluctuations between the electrical contacts 640, 645. The program instructions 672 could additionally include instructions to operate other elements of the signal conditioner 630 (e.g., switches, circuit breakers, FETs) to protect other elements of the wearable device 600 that are electrically coupled to the electrical contacts 640, 645 (e.g., an amplifier and/or voltage sensor of the signal conditioner 630) from being damaged. The program instructions 672 could include instructions to operate based on parameter and user data 674 stored in the computer readable medium 660 and/or modify the parameters and user data 674. For example, the parameters and user data 674 could include calibration data for the wearable device 600 and/or stored ECG waveforms (and/or features thereof, e.g., Q-T intervals, QRS complex parameters) extracted using the wearable device 600.

The program instructions 672 stored on the computer readable medium 660 could include instructions for operating the signal conditioner 630 to extract an ECG waveform from voltage fluctuations between the electrical contacts 640, 645. The instructions could include instructions to activate and/or set a value of a current source, a voltage source, a programmable resistor, an ADC, one or more electronic switches, and/or some other component(s) of the signal conditioner 630. The instructions could include instructions to set a gain, bandwidth, corner frequency, notch frequency, or other property of an amplifier and/or filter of the signal conditioner 630. The instructions could include instructions to operate a voltage or current sensor to make one or more measurements relating to the voltage between the electrical contacts 640, 645. The instructions could include instructions to operate a voltage or current sensor to make a series of measurements during a respective series of regularly spaced periods of time relating to the voltage between the electrical contacts 640, 645.

The instructions could include instructions to determine whether the first and second electrical contacts 640, 645 are in contact with skin and/or that an ECG waveform can be extracted from voltage fluctuations between electrical contacts 640, 645 and to responsively extract an ECG waveform. This could include analyzing voltage fluctuations between the electrical contacts 640, 645 to determine whether the voltage fluctuations contain ECG waveforms. Additionally or alternatively, this could include actively or passively sensing an effective resistance and/or capacitance between the electrical contacts 640, 645 and further determining that the sensed resistance and/or capacitance corresponds to the electrical contacts 640, 645 being in contact with skin. In some examples, the instructions could include instructions to extract an ECG waveform in response to a user input (e.g., in response to a user depressing a button of the wearable device 600 to indicate that the wearer is contacting the first and second electrical contacts 640, 645 to skin at appropriate respective first and second skin locations).

Other instructions in the program instructions 672 relating to the use of the signal conditioner 630 to extract one or more ECG waveforms from voltage fluctuations between the electrical contacts 640, 645 are anticipated. The program instructions 672 could include instructions to extract a plurality of ECG waveforms during a plurality of periods of time using the signal conditioner 630. The program instructions 672 could include instructions to log or otherwise store data related to the extracted ECG waveform(s) in the parameters and user data 874 and/or some other data storage.

The instructions could include instructions to operate the wearable device 600 based on an extracted ECG waveform(s) and or information related to extracted ECG waveform(s). For example, the instructions could describe how to determine a health or other state of a wearer based on extracted ECG waveform(s) (e.g., based on a determined heart rate, a determine pulse timing variability, a determined Q-T interval, determined QRS complex parameters, or some other determined property or feature of one or more extracted ECG waveforms). The instructions could describe how to determine whether the first and second electrical contacts 640, 645 are in contact with skin and/or that an ECG waveform can be extracted from voltage fluctuations between them 640, 645. The instructions could further describe how to operate the wearable device 600 relative to such a determination. For example, one or more elements (e.g., a voltage or current sensor, an amplifier) of the signal conditioner 630 and/or of the wearable device 600 could be disabled and/or operated in a low-power state when the wearable device 600 determines that the first and second electrical contacts 640, 645 are not in contact with skin and/or that an ECG waveform cannot be extracted from voltage fluctuations between them 640, 645. Other operations relative to such a determination are anticipated and could be described by the program instructions 672.

The program instructions 672 stored on the computer readable medium 660 could include instructions for operating components of the wearable device 600 (e.g., the signal conditioner 630) to recharge the rechargeable battery 635 and/or to power the wearable device 600 using the rechargeable battery 635. For example, the instructions could include instructions for operating switches or other electrical components to gate power from the electrical contacts 640, 645 to the recharger and/or from the recharger to the rechargeable battery 635. Additionally or alternatively, the instructions could include instructions to operate a voltage or current sensor (possibly a sensor of the signal conditioner 630) to detect the presence of an external charger in electrical contact with the electrical contacts 640, 645 and/or to detect a charge state of the rechargeable battery 635. A recharger and/or rectifier elements of the signal conditioner 630 or of other electronics of the wearable device 600 could be passive, that is, they could be configured to recharge the rechargeable battery 635 and/or power the wearable device 600 without direct operation by the processor(s) 650 or other elements of the wearable device 600 (other than the electrical contacts 640, 645) when the wearable device 600 is mounted to an external charger or other appropriately configured power source. Additionally or alternatively, a coil and other components of a wireless charger of the wearable device 600 could be configured to receive electromagnetic energy and to charge the rechargeable battery 635 using the received electromagnetic energy.

The program instructions 672 can include instructions for operating the user interface(s) 680. For example, the program instructions 672 could include instructions for displaying data about the wearable device 600, for displaying an extracted ECG waveform or other information generated by the wearable device 600 (e.g., a heart rate, a variability of extracted ECG waveforms), or for displaying one or more alerts generated by the wearable device 600 and/or received from an external system. Further, program instructions 672 may include instructions to execute certain functions based on inputs accepted by the user interface(s) 680, such as inputs accepted by one or more buttons disposed on the user interface(s) 680.

Communication interface 690 may also be operated by instructions within the program instructions 672, such as instructions for sending and/or receiving information via an antenna, which may be disposed on or in the wearable device 600. For example, the program instructions 672 could include instructions to operate the communication interface 690 to transmit an extracted ECG waveform and/or information related to an extracted ECG waveform using the communication interface 690 (e.g., using a wireless transmitter of the communication interface 690). The communication interface 690 can optionally include one or more oscillators, mixers, frequency injectors, etc. to modulate and/or demodulate information on a carrier frequency to be transmitted and/or received by the antenna. In some examples, the wearable device 600 is configured to indicate an output from the processor 650 by modulating an impedance of the antenna in a manner that is perceivable by a remote server or other remote computing device.

In some examples, the communication interface(s) 690 could be operably coupled to the electrical contacts 640, 645 and could be configured to communicate with an external system by using the electrical contacts 640, 645. In some examples, this includes sending and/or receiving voltage and/or current signals transmitted through the electrical contacts 640, 645 when the wearable device 600 is mounted onto an external system such that the electrical contacts 640, 645 are in electrical contact with components of the external system.

In some examples, extracted ECG waveforms, temperature measurements, wearer profiles, history of wearable device use, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, extracted ECG waveforms and/or health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by instructions contained in the program instructions 672 that a medical condition is indicated, the wearable device 600 may generate an alert via the user interface 680. The alert may include a visual component, such as textual or graphical information displayed on a display, an auditory component (e.g., an alarm sound), a tactile component (e.g., a vibration), and/or an electro-haptic component (e.g., an electro-haptic stimulus delivered using the electrical contacts 640, 645). The textual information may include one or more recommendations, such as a recommendation that the wearer of the device contact a medical professional, seek immediate medical attention, or administer a medication.

V. Illustrative Methods for Operating a Wearable Device

Figure 7:
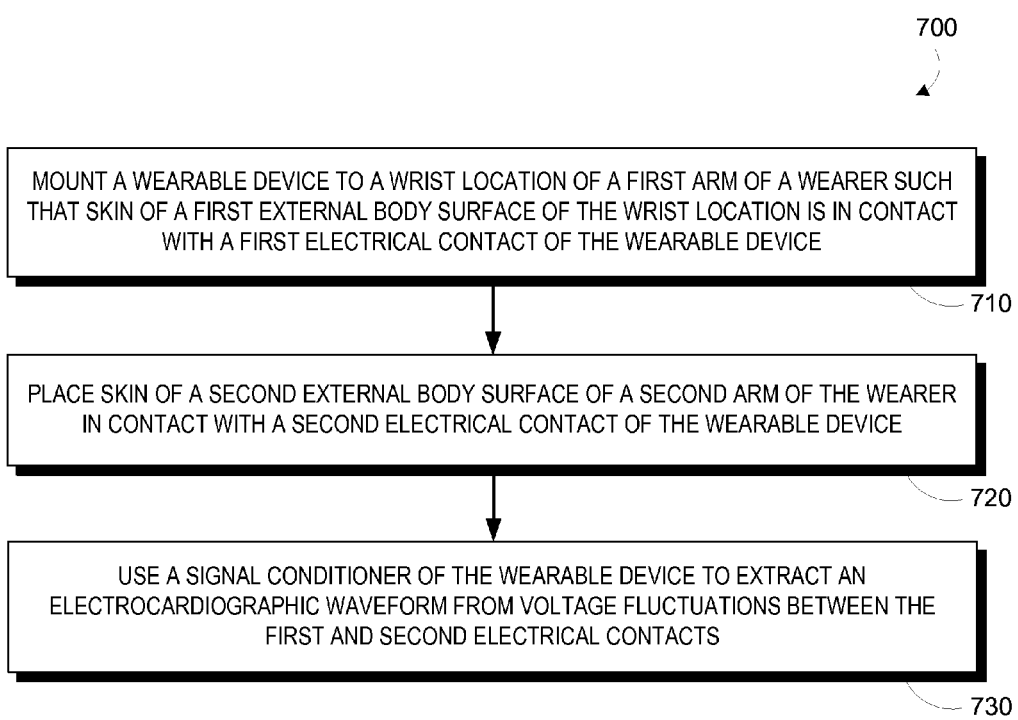
FIG. 7 is a flowchart of an example method.

FIG. 7 is a flowchart of a method 700 for operating a wearable device. The operated wearable device includes (i)

a housing, (ii) a mount configured to mount the housing to a wrist location of a first arm of a wearer, (iii) a first electrical contact disposed on the housing and configured to contact skin at a first external body surface when the housing is mounted on the first external body surface, (iv) a second electrical contact that is configured to be contacted by skin of a second body surface located on a second arm of the wearer, (v) a signal conditioner connected to the first and second electrical contacts and configured to extract an electrocardiographic (ECG) waveform form voltage fluctuations between the first and second electrical contacts.

The method 700 includes mounting the wearable device to the wrist location of the first arm of the wearer such that skin of the first external body surface of the wrist location is in contact with the first electrical contact (710). This could include encircling the wrist of the wearer with a band, strap, or other encircling element of the mount. This could include operating a clasp, snap, or other securing elements of the mount such that the wearable device is mounted to the wrist location (e.g., securing two halves of a flexible strap of the mount together around the wrist of the wearer). In some examples, the mount includes an adhesive, and mounting the wearable device to the wrist location (710) includes activating, applying, and/or exposing the adhesive and adhering the wearable device to the wrist location.

The method 700 also includes placing skin of the second external body surface of a second arm of the wearer in contact with the second electrical contact (720). This could include the wearer contacting the second electrical contact with skin of one or more of a finger, hand, wrist, or forearm of the second arm. Placing skin of the second external body surface in contact with the second electrical contact (720) could occur at the initiative of the wearer, e.g., in response to the wearer having performed and/or being about to perform a strenuous task (e.g., exercise), experiencing some symptoms (e.g., fatigue, nausea, vertigo, heart palpitations, orthostatic hypertension), having received and/or being about to receive a drug (e.g., having taken nitroglycerin). Additionally or alternatively, placing skin of the second external body surface in contact with the second electrical contact (720) could occur in response to an indication (e.g., a vibration, a sound, a visual indication on a display of the wearable device, an indication through some other device in communication with the wearable device) that the wearer should perform such an action to enable the extraction of an ECG waveform by the wearable device.

The method 700 also includes using the signal conditioner of the wearable device to extract an ECG waveform from voltage fluctuations between the first and second electrical contacts (730). This could include sampling (e.g., using an ADC or other discrete-time device) a voltage between the first and second electrical contacts a plurality of time during a plurality of respective points in time. This could include amplifying, filtering, level-shifting, inverting, and/or performing some other operation on the voltage between the first and second electrical contacts using, e.g., one or more amplifiers, filters, op-amps, resistors, inductors, capacitors, other electronic element(s), and/or combinations thereof.

The method 700 for operating a wearable device could include additional steps relating to an extracted ECG waveform. In some examples, the method 700 could include indicating the extracted ECG waveform and/or information related to the ECG waveform using a display disposed in the wearable device. In some examples, the method 700 could include wirelessly transmitting the extracted ECG waveform and/or information related to the ECG waveform using a wireless transmitter disposed in the wearable device. For example, the wearable device could transmit an extracted ECG waveform to a remote system (e.g., a server or cloud service accessible to a healthcare provider). In some examples, the method 700 could include logging or otherwise storing the extracted ECG waveform and/or information related to the ECG waveform using a data storage disposed in the wearable device. In some examples, the method 700 could include operating the wearable device based on the extracted ECG waveform and/or information related to the ECG waveform. For example, the wearable device could be operated to generate an alert, send a transmission to a remote system, or some other action in response to the extracted ECG waveform and/or information related to the ECG waveform (e.g., if a Q-T interval of the extracted ECG waveform exceeds a threshold).

In another example, the method 700 could include determining whether the first and second electrical contacts are in contact with skin at the first and second external body surfaces, respectively. For example, the method could include determining that electrical contacts are contacting respective skin locations based on a detected capacitance and/or resistance between the electrical contacts being within a specified range and/or increasing or decreasing at a specified rate. The method could further include operating the wearable device relative to such a determination. For example, extracting an ECG waveform using the signal conditioner (730) could be performed in response to the determination that the first and second electrical contacts are in contact with respective first and second external body surfaces. Other applications of a determined resistance and/or capacitance are anticipated.

In some examples, the wearable device could include means for optically detecting the volume of blood in a portion of subsurface vasculature of the wearer at a plurality of points in time, and generating a blood volume waveform over time (i.e., a photoplethysmographic waveform) based on the plurality of detected volumes of blood. An individual such blood volume detection could include operating a light source of the wearable device to emit light into the portion of subsurface vasculature through overlying skin and operating a light sensor of the wearable device to receive light responsively reflected, scattered, or otherwise emitted from the portion of subsurface vasculature through the overlying skin. The method 700 could further include using the generated blood volume waveform, in combination with the extracted ECG waveform, to determine a blood pressure of the wearer, a degree of atherosclerosis of the vasculature of the wearer, or some other health or medical state of the wearer. This could include determining time differences or other comparisons of features of the extracted ECG waveform and the generated blood volume waveform (e.g., a time difference between a maximum of the volume waveform and a corresponding QRS complex of the ECG waveform) to determine a flow rate, a pressure wave speed and/or latency, or other information about the blood in the portion of subsurface vasculature and/or information about the heart and vasculature of the wearer.

The example method 700 illustrated in FIG. 7 is meant as an illustrative, non-limiting example. Additional or alternative elements of the method and additional or alternative components of the wearable device are anticipated, as will be obvious to one skilled in the art.

IV. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A wearable device, comprising:
   a housing;
   a modular mount for mounting the housing to a first external body surface, wherein the first external body surface is a wrist location of a first arm of a wearer, wherein the modular mount comprises a band and a frame, wherein the housing is removably seated in the frame, and wherein the band can encircle a wrist of the first arm of the wearer;
   a first electrical contact disposed on the housing, wherein the first electrical contact contacts skin at the first external body surface when the housing is mounted on the first external body surface;
   a second electrical contact disposed on an outside surface of the modular mount, wherein the second electrical contact can be contacted by skin of a second external body surface, wherein the second external body surface is a location of a second arm of the wearer; and
   a signal conditioner disposed in the housing and electrically connected to the first and second electrical contacts, wherein the signal conditioner extracts an electrocardiographic waveform from voltage fluctuations between the first electrical contact and the second electrical contact;
   wherein the signal conditioner is in electrical contact with the second electrical contact when the housing is seated in the frame, and wherein unseating the housing from the frame removes electrical contact between the signal conditioner and the second electrical contact.

2. The wearable device of claim 1, wherein the signal conditioner is in electrical contact with the second electrical contact via at least one spring-loaded contact, wherein the spring loaded contact is disposed in the wearable device such that it is compressed when the housing is seated in the frame.

3. The wearable device of claim 1, further comprising a display, wherein the display is disposed on an outside surface of the housing, and wherein the second electrical contact is disposed proximate to a peripheral edge of the display and at least partially encircles the display.

4. The wearable device of claim 1, wherein the second electrical contact is disposed on an outside surface of the band.

5. The device of claim 1, wherein at least one of the first and second electrical contacts has a surface comprising silver/silver-chloride.

6. The device of claim 1, wherein at least one of the first and second electrical contacts capacitively couples to skin at the first and second locations, respectively.

7. The device of claim 1, further comprising a wireless transmitter that transmits data related to the extracted electrocardiographic waveform.

8. The device of claim 1, further comprising a data storage that logs data related to the extracted electrocardiographic waveform.

9. The device of claim 1, wherein the signal conditioner comprises at least one amplifier, at least one high-pass filter, and at least one low-pass filter.

10. The device of claim 9, wherein the signal conditioner comprises fast recovery circuitry, wherein the fast recovery circuitry detects when the signal conditioner is electronically saturated and responsively controls one or more properties of the signal conditioner to reduce the electronic saturation of the signal conditioner.

11. The device of claim 1, further comprising a further sensor.

12. The device of claim 11, wherein the further sensor comprises a light source and a light sensor, and wherein the further sensor detects a volume of blood in subsurface vasculature by emitting light into the subsurface vasculature through an overlying skin location and receiving light from the subsurface vasculature through the overlying skin location.

13. The device of claim 1, wherein the signal conditioner determines whether the first and second electrical contacts are in contact with skin at the first and second external body surfaces, respectively.

14. A method comprising:
    mounting a wearable device to a wrist of a first arm of a wearer, wherein the device comprises:
      a housing;
      a modular mount, wherein the modular mount comprises a band and a frame, wherein mounting the wearable device to the wrist comprises removably seating the housing in the frame and encircling the band around the wrist;

a first electrical contact disposed on the housing, wherein the first electrical contact contacts skin at a first external body surface when the wearable device is mounted to the wrist;

a second electrical contact disposed on an outside surface of the modular mount, wherein the second electrical contact can be contacted by skin of a second external body surface, wherein the second external body surface is a location of a second arm of the wearer; and a signal conditioner disposed in the housing and electrically connected to the first and second electrical contacts, wherein the signal conditioner extracts an electrocardiographic waveform from voltage fluctuations between the first electrical contact and the second electrical contact;

wherein removably seating the housing in the frame causes the signal conditioner to be in electrical contact with the second electrical contact, and wherein unseating the housing from the frame removes electrical contact between the signal conditioner and the second electrical contact;

while the wearable device is mounted to the wrist location of the first arm of the wearer such that the first electrical contact is in contact with skin at the first external body surface, placing skin of the second external body surface in contact with the second electrical contact; and while the first electrical contact is in contact with skin at the first external body surface and the second electrical contact is in contact with skin of the second external body surface, using the signal conditioner to extract the electrocardiographic waveform.

15. The method of claim 14, further comprising indicating information related to the extracted electrocardiographic waveform using a display disposed in the wearable device.

16. The method of claim 14, wherein the device further comprises a wireless transmitter, and further comprising:

transmitting data related to the extracted electrocardiographic waveform using the wireless transmitter.

17. The device of claim 14, wherein the device further comprises a data storage, and further comprising:

logging data related to the extracted electrocardiographic waveform using the data storage.

18. The method of claim 14, wherein the device further comprises a light source and a light sensor, and further comprising:

operating the light source to emit light into subsurface vasculature of the wearer through an overlying skin location of the wearer;

operating the light sensor to receive light from the subsurface vasculature through the overlying skin location;

determining a photoplethysmographic signal related to the volume of blood in the subsurface vasculature based at least on the light received from the subsurface vasculature by the light sensor; and determining a blood pressure of the wearer based at least on the determined photoplethysmographic signal and the extracted electrocardiographic waveform.

19. The method of claim 14, wherein the signal conditioner can further determine whether the first and second electrical contacts are in contact with skin at the first and second external body surfaces, respectively, and further comprising:

determining, using the signal conditioner, that the first and second electrical contacts are in contact with skin at the first and second external body surfaces, respectively.

20. The method of claim 14, wherein removably seating the housing in the frame causes the signal conditioner to be in electrical contact with the second electrical contact via at least one spring-loaded contact, wherein the spring loaded contact is disposed in the wearable device such that it is compressed when the housing is seated in the frame.

* * * * *